(12) United States Patent
Hazra et al.

(10) Patent No.: US 12,399,254 B2
(45) Date of Patent: Aug. 26, 2025

(54) RADAR-BASED SINGLE TARGET VITAL SENSING

(71) Applicants: Infineon Technologies AG, Neubiberg (DE); Friedrich-Alexander-Universität Erlangen-Nürnberg, Erlangen (DE)

(72) Inventors: Souvik Hazra, Munich (DE); Avik Santra, Munich (DE); Thomas Reinhold Stadelmayer, Wenzenbach (DE)

(73) Assignee: Infineon Technologies AG, Neubiberg (DE)

( * ) Notice: Subject to any disclaimer, the term of this patent is extended or adjusted under 35 U.S.C. 154(b) by 391 days.

(21) Appl. No.: 17/834,557

(22) Filed: Jun. 7, 2022

(65) Prior Publication Data

US 2023/0393259 A1      Dec. 7, 2023

(51) Int. Cl.
*G01S 7/41*      (2006.01)
*G01S 7/35*      (2006.01)

(52) U.S. Cl.
CPC ............. *G01S 7/415* (2013.01); *G01S 7/358* (2021.05); *G01S 7/411* (2013.01); *G01S 7/417* (2013.01)

(58) Field of Classification Search
CPC ......... G01S 7/415; G01S 7/358; G01S 7/411; G01S 7/417; G01S 13/56; A61B 5/024;

(Continued)

(56) References Cited

U.S. PATENT DOCUMENTS 4,241,347 A    12/1980   Albanese et al.
6,147,572 A    11/2000   Kaminski et al.
(Continued)

FOREIGN PATENT DOCUMENTS

CN      1463161 A     12/2003
CN      1716695 A      1/2006
(Continued)

OTHER PUBLICATIONS

Jang, Y.I.; Sim, J.Y.; Yang, J.-R.; Kwon, N.K. The Optimal Selection of Mother Wavelet Function and Decomposition level for Denoising of DCG Signal. Sensors 2021, 21, 1851. https://doi.org/ 10.3390/s21051851 (Year: 2021).*

(Continued)

*Primary Examiner* — Matthew M Barker
(74) *Attorney, Agent, or Firm* — Slater Matsil, LLP

(57) ABSTRACT

In an embodiment, a method includes: generating a target displacement signal indicative of a movement of a human target based on raw digital data generated by a millimeter-wave radar sensor; and estimating a vital sign of the human target based on the target displacement signal, where generating the target displacement signal includes: generating target in-phase (I) and quadrature (Q) (I/Q) data associated with the human target based on the raw digital data, classifying the target I/Q data as high quality data or as low quality data using a first neural network, when the target I/Q data is classified as low quality data, discarding the target I/Q data, when the target I/Q data is classified as high quality data, performing ellipse fitting on the target I/Q data to generate compensated I/Q data, and generating the target displacement signal based on the compensated I/Q data.

24 Claims, 11 Drawing Sheets

(58) Field of Classification Search
CPC ... A61B 5/0816; A61B 5/7257; A61B 5/0507; A61B 5/113
See application file for complete search history.

(56) References Cited

U.S. PATENT DOCUMENTS

| | | |
|---|---|---|
| 6,414,631 B1 | 7/2002 | Fujimoto |
| 6,636,174 B2 | 10/2003 | Arikan et al. |
| 7,048,973 B2 | 5/2006 | Sakamoto et al. |
| 7,057,564 B2 | 6/2006 | Tsai et al. |
| 7,171,052 B2 | 1/2007 | Park |
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,477,812 B2 | 10/2016 | Lin et al. |
| 9,495,600 B2 | 11/2016 | Heu et al. |
| 9,886,095 B2 | 2/2018 | Pothier |
| 9,935,065 B1 | 4/2018 | Baheti et al. |
| 10,601,630 B1 | 3/2020 | Dickerman et al. |
| 10,795,012 B2 | 10/2020 | Santra et al. |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0074307 A1 | 3/2008 | Boric-Lubecke et al. |
| 2008/0077015 A1 | 3/2008 | Boric-Lubecke et al. |
| 2008/0106460 A1 | 5/2008 | Kurtz et al. |
| 2008/0119716 A1 | 5/2008 | Boric-Lubecke et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0152600 A1 | 6/2010 | Droitcour et al. |
| 2010/0207805 A1 | 8/2010 | Haworth |
| 2011/0299433 A1 | 12/2011 | Darabi et al. |
| 2012/0022348 A1 | 1/2012 | Droitcour et al. |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0215734 A1 | 8/2017 | Yamaji |
| 2017/0364160 A1 | 12/2017 | Malysa et al. |
| 2018/0046255 A1 | 2/2018 | Rothera et al. |
| 2018/0055451 A1 | 3/2018 | Kuroyanagi et al. |
| 2018/0071473 A1 | 3/2018 | Trotta et al. |
| 2018/0101239 A1 | 4/2018 | Yin et al. |
| 2018/0279884 A1 | 10/2018 | Ahmad et al. |
| 2019/0302252 A1 | 10/2019 | Santra et al. |
| 2020/0113445 A1 | 4/2020 | Gigie et al. |
| 2020/0367764 A1 | 11/2020 | Le Guillou et al. |
| 2021/0255280 A1 | 8/2021 | Santra et al. |
| 2021/0325509 A1 | 10/2021 | Santra et al. |
| 2021/0398666 A1* | 12/2021 | Maslik .................. A61B 5/4842 |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| CN | 203950036 U | 11/2014 |
| CN | 106644030 A | 5/2017 |
| CN | 110065499 A | 7/2019 |
| DE | 102008054570 A1 | 6/2010 |
| DE | 102011100907 A1 | 1/2012 |
| DE | 102011075725 A1 | 11/2012 |

(56) References Cited

FOREIGN PATENT DOCUMENTS

| | | |
|---|---|---|
| DE | 102014118063 A1 | 7/2015 |
| EP | 3869222 A1 | 8/2021 |
| EP | 3901651 A1 | 10/2021 |
| EP | 3926361 A2 | 12/2021 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

OTHER PUBLICATIONS

M. Ravanelli and Y. Bengio, "Speaker Recognition from Raw Waveform with SincNet," 2018 IEEE Spoken Language Technology Workshop (SLT), Athens, Greece, 2018, pp. 1021-1028, doi: 10.1109/SLT.2018.8639585. (Year: 2018).*

"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.

Chen, Xiaolong et al., "Detection and Extraction of Marine Target with Micromotion via Short-Time Fractional Fourier Transform in Sparse Domain," IEEE International Conference on Signal Processing, Communications and Computing, CSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, pp. 1847-1855.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:\\dooringalertsystems.com, printed Oct. 4, 2017, 16 pages.

Filippelli, Mario et al., "Respiratory dynamics during laughter," J Appl Physiol, (90), 1441-1446, Apr. 2001, http://iap.physiology.org/content/jap/90/4/1441.full.pdf.

Fox, Ben, "The Simple Technique That Could Save Cyclists' Lives," https://www.outsideonline.com/2115116/simple-technique-could-save-cyclists-lives, Sep. 19, 2016, 6 pages.

Gigie, Andrew et al., "Novel Approach for Vibration Detection Using Indented Radar", Progess in Electromagnetic Research C, vol. 87, pp. 147-162, Oct. 4, 2018.

Gouveia, Carolina et al., "A Review on Methods for Random Motion Detection and Compensation in Bio-Radar Systems", Sensors, MDPI, Jan. 31, 2019, 17 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Gu, Changzhan et al., "Deep Neural Network based Body Movement Cancellation for Doppler Radar Vital Sign Detection", IEEE MTT-S International Wireless Symposium (IWS) May 19-22, 2019, 3 pages.

Gu, Changzu "Short-Range Noncontact Sensors for Healthcare and Other Emerginng Applications: A Review", Sensors, MDPI, Jul. 26, 2016, 24 pages.

Gu, Changzhan et al., "From Tumor Targeting to Speed Monitoring", IEEE Microwave Magazine, ResearchGate, Jun. 2014, 11 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, pp. 725-735.

Immoreev, I. Ya. "Ultrawideband Radars: Features and Capabilities", Journal of Communications Technology and Electronics, ISSN: 1064-2269, vol. 54, No. 1, Feb. 8, 2009, pp. 1-26.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWR1xxx Power Management Optimizations—Low Cost LC Filter Solution," Application Report SWRA577, Texas Instruments, Oct. 2017, 19 pages.

Kishore, N. et al., "Millimeter Wave Antenna for Intelligent Transportation Systems Application", Journal of Microwaves, Optoelectronics and Electromagnetic Applications, vol. 17, No. 1, Mar. 2018, pp. 171-178.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Li, Changzhi et al., "A Review on Recent Advances in Doppler Radar Sensors for Noncontact Healthcare Monitoring", IEEE Transactions on Microwave Theory and Techniques, vol. 61, No. 5, May 2013, pp. 2046-2060.

Li, Changzhi et al., "A Review on Recent Progress of Portable Short-Range Noncontact Microwave Radar Systems", IEEE Transactions on Microwave Theory and Techniques, vol. 65, No. 5, May 2017, pp. 1692-1706.

Zakrzewski, M. et al., "Quadrature Imbalance Compensation with Ellipse-Fitting Methods for Microwave Radar Physiological Sensing," IEEE Transactions on Microwave Theory and Techniques, vol. 62, No. 6, Jun. 2014, 10 pages.

Li, Changzhi et al., "Random Body Movement Cancellation in Doppler Radar Vital Sign Detection", IEEE Transactions on Microwave Theory and Techniques, vol. 56, No. 12, Dec. 2008, pp. 3143-3152.

Li, Changzi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.

Li, Changzhi "Vital-sign monitoring on the go", Sensors news and views, www.nature.com/naturelectronics, Nature Electronics, vol. 2, Jun. 2019, 2 pages.

Lim, Soo-Chul et al., "Expansion of Smartwatch Touch Interface from Touchscreen to Around Device Interface Using Infrared Line

(56) References Cited

OTHER PUBLICATIONS

Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, pp. 2542-2549.

Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Mostov, K., et al., "Medical applications of shortwave FM radar: Remote monitoring of cardiac and respiratory motion", Am. Assoc. Phys. Med., 37(3), Mar. 2010, pp. 1332-1338.

Oguntala, G et al., "Indoor location identification technologies for real-time IoT-based applications: an inclusive survey", Elsevier Inc., http://hdl.handle.net/10454/16634, Oct. 2018, 42 pages.

Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, pp. 747-757.

Santra, Avik et al., "Short-range multi-mode continuous-wave radar for vital sign measurement and imaging", ResearchGate, Conference Paper, Apr. 2018, 6 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Singh, Aditya et al., "Data-Based Quadrature Imbalance Compensation for a CW Doppler Radar System", ResearchGate, https://www.researchgate.net/publication/258793573, IEEE Transactions on Microwave Theory and Techniques, Apr. 2013, 7 pages.

Suleymanov, Suleyman, "Design and Implementation of an FMCW Radar Signal Processing Module for Automotive Applications," Master Thesis, University of Twente, Aug. 31, 2016, 61 pages.

Thayaparan, T. et al., "Micro-Doppler Radar Signatures for Intelligent Target Recognition," Defence Research and Development Canada, Technical Memorandum, DRDC Ottawa™ 2004-170, Sep. 2004, 73 pages.

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Tu, Jianxuan et al., "Fast Acquisition of Heart Rate in Noncontact Vital Sign Radar Measurement Using Time-Window-Variation Technique", IEEE Transactions on Instrumentation and Measurement, vol. 65, No. 1, Jan. 2016, pp. 112-122.

Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.

Vinci, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, pp. 2093-2100.

Wang, Fu-Kang et al., "Wrist Pulse Rate Monitor Using Self-Injection-Locked Radar Technology", Biosensors, MDPI, Oct. 26, 2016, 12 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Will, Christoph et al., "Advanced Template Matching Algorithm for Instantaneous Heartbeat Detection using Continuous Wave Radar Systems", ResearchGate, May 2017, 5 pages.

Will, Christoph et al., "Human Target Detection, Tracking, and Classification Using 24-GHz FMCW Radar", IEEE Sensors Journal, vol. 19, No. 17, Sep. 1, 2019, pp. 7283-7299.

Will, Christoph et al., "Local Pulse Wave Detection using Continuous Wave Radar Systems", IEEE Journal of Electromagnetics, RF and Microwaves in Medicine and Biology, Oct. 25, 2017, 9 pages.

Will, Christoph et al., "Radar-Based Heart Sound Detection", Scientific Reports, www.nature.com/scientificreports, Jul. 26, 2018, 15 pages.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.

\* cited by examiner

RADAR-BASED SINGLE TARGET VITAL SENSING

CROSS-REFERENCE TO RELATED APPLICATIONS

This application is related to co-pending U.S. patent application Ser. No. 16/853,011, filed on Apr. 20, 2020, entitled "Radar-Based Vital Sign Estimation," and associated with and to co-pending U.S. patent application Ser. No. 16/794,904, filed on Feb. 19, 2020 entitled "Radar Vital Signal Tracking Using a Kalman Filter," which applications are hereby incorporated herein by reference.

TECHNICAL FIELD

The present disclosure relates generally to an electronic system and method, and, in particular embodiments, to a radar-based single target vital sensing.

BACKGROUND

Applications in the millimeter-wave frequency regime have gained significant interest in the past few years due to the rapid advancement in low cost semiconductor technologies, such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at e.g., 24 GHz, 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal (also referred to as the echo), and determining a distance based on a time delay and/or frequency difference between the transmission and reception of the frequency modulated signal. Accordingly, some radar systems include a transmit antenna to transmit the radio-frequency (RF) signal, and a receive antenna to receive the reflected RF signal, as well as the associated RF circuits used to generate the transmitted signal and to receive the RF signal. In some cases, multiple antennas may be used to implement directional beams using phased array techniques. A multiple-input and multiple-output (MIMO) configuration with multiple chipsets can be used to perform coherent and non-coherent signal processing as well.

SUMMARY

In accordance with an embodiment, a method includes: transmitting radar signals using a millimeter-wave radar sensor; receiving reflected radar signals using the millimeter-wave radar sensor; generating raw digital data based on the reflected radar signals; generating a target displacement signal indicative of a movement of a human target based on the raw digital data; and estimating a vital sign of the human target based on the target displacement signal, where generating the target displacement signal includes: generating target in-phase (I) and quadrature (Q) (I/Q) data associated with the human target based on the raw digital data, classifying the target I/Q data as high quality data or as low quality data using a first neural network, when the target I/Q data is classified as low quality data, discarding the target I/Q data, when the target I/Q data is classified as high quality data, performing ellipse fitting on the target I/Q data to generate compensated I/Q data, and generating the target displacement signal based on the compensated I/Q data.

In accordance with an embodiment, a radar system includes: a millimeter-wave radar sensor including: a transmitter configured to transmit radar signals, a receiver configured to receive reflected radar signals, and an analog-to-digital converter (ADC) configured to generate raw digital data based on the reflected radar signals; and a processing system configured to: generate target in-phase (I) and quadrature (Q) (I/Q) data associated with a human target based on the raw digital data, classify the target I/Q data as high quality data or as low quality data using a first neural network, when the target I/Q data is classified as low quality data, discard the target I/Q data, when the target I/Q data is classified as high quality data, perform ellipse fitting on the target I/Q data to generate compensated I/Q data, generate a target displacement signal indicative of a movement of the human target, and estimate a heartbeat rate of the human target based on the target displacement signal.

In accordance with an embodiment, a method includes: transmitting radar signals using a millimeter-wave radar; receiving reflected radar signals using the millimeter-wave radar; generating raw digital data based on the reflected radar signals; generating a target displacement signal indicative of a movement of a human target based on the raw digital data; performing wavelet denoising on the target displacement signal to generate a denoised displacement signal; using an adaptive Sinc filter to generate a heartbeat filtered displacement signal based on the denoised displacement signal; and estimating a heartbeat rate of the human target based on the heartbeat filtered displacement signal.

In accordance with an embodiment, a method includes: transmitting radar signals using a millimeter-wave radar sensor; receiving reflected radar signals using the millimeter-wave radar sensor; generating raw digital data based on the reflected radar signals; determining a number of people within a field-of-view of the millimeter-wave radar sensor based on the raw digital data; when the number of people is equal to 1, using a vital sensing pipeline to generate a target displacement signal indicative of a movement of a human target based on the raw digital data, and estimate a vital sign of the human target based on the target displacement signal; and when the number of people is greater equal to 0, disabling the vital sensing pipeline.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

Figure 1:
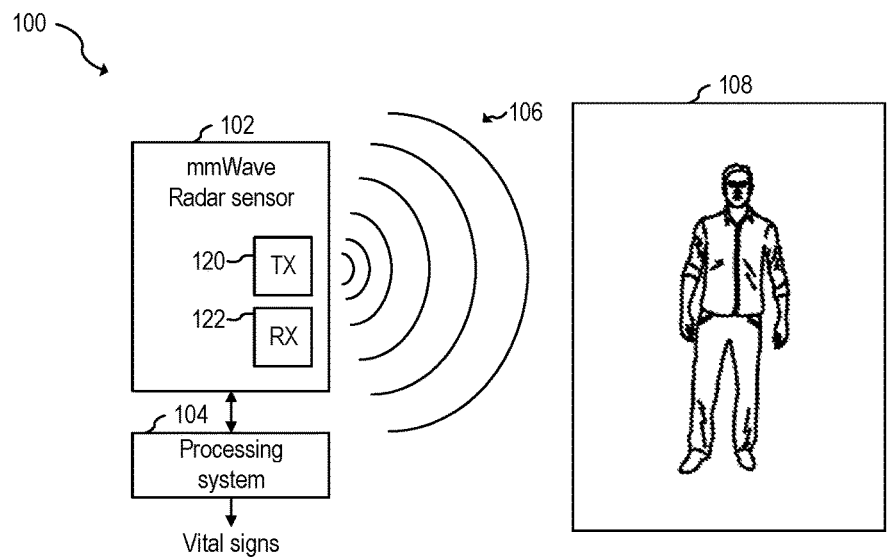
FIG. 1 shows a radar system, according to an embodiment of the present invention.

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in specific contexts, e.g., a radar-based system and method for estimating vital signs (such as respiration rate and heartbeat rate) for a single human target. Embodiments of the present invention may be used for estimating vital signs of a non-human target (such as an animal). Some embodiments may be used for post-processing purposes after extracting individual target I/Q data, e.g., in a multi-person scenario.

Embodiments of the present invention may be used in a variety of applications. For example, some embodiments may be used for patient monitoring in hospitals. Some embodiments may be used for sleep monitoring, e.g., at home. Some embodiments may be used for monitoring a user in front of a television or laptop. Some embodiments may be used for monitoring a driver of a car. Other applications are also possible.

In an embodiment of the present invention, a vital sign (e.g., heartbeat rate, respiration rate) of a single human target is estimated (e.g., continuously) using a millimeter-wave radar system. A Good/Bad classifier is used to distinguish between high quality I/Q data and low quality I/Q data associated with the human target. A displacement signal is generated based on the high quality I/Q data, and an adaptive set of Sinc filters filter the displacement signal to generate a filtered displacement signal. The vital sign is then estimated based on the filtered displacement signal. In some embodiments, the vital sensing pipeline that estimates the vital signs of the human target is enabled or disabled based on the number of people present in a field-of-view (FoV) of the millimeter-wave radar system.

A radar, such as a millimeter-wave radar, may be used to detect a human target and track vital signs (such as heartbeat rate and respiration rate) of the detected human target. In some embodiments, therefore, a radar, such as a millimeter-wave radar, enables a contactless, non-invasive method for vital sensing, which may advantageously increase the comfort of the human target during the vital signs monitoring. Some embodiments allow for continuous monitoring of vital signs, which may advantageously allow for detecting critical health conditions in a timely manner.

Conventionally, radar-based vital sensing utilizes the discrete Fourier transform and determines respiration rate and heartbeat rate by detecting the maximum peaks in the frequency spectrum. Such an approach may be susceptible to multiple reflections, multipath effects, motion artifacts, random body movements (RBM) and intermodulation product (IMP), for example. For example, IMP at a frequency of $f_h+f_r$ may occur between the heartbeat rate (e.g., at a heartbeat frequency $f_h$ between 0.7 Hz and 3 Hz) and a respiration rate (e.g., at a respiration frequency $f_r$ between 0.2 Hz and 0.5 Hz).

FIG. 1 shows radar system 100, according to an embodiment of the present invention. Radar system 100 includes millimeter-wave radar sensor 102 and processing system 104.

During normal operation, millimeter-wave radar sensor 102 transmits a plurality of radar signals 106, such as chirps, towards scene 108 using transmitter (TX) circuit 120. In some embodiments the chirps are linear chirps (i.e., the instantaneous frequency of the chirp varies linearly with time).

The transmitted radar signals 106 are reflected by objects in scene 108. The reflected radar signals (not shown in FIG. 1), which are also referred to as the echo signal, are received by millimeter-wave radar sensor 102 using receiver (RX)

circuit 122 and processed by processing system 104 to, for example, detect a human target and track the vital signs of the detected human target.

The objects in scene 108 may include one or more humans. Other objects, such as furniture and walls, and periodic movement equipment, such as fans, may also be present in scene 108.

Generally, monitoring vital signs, such as heartbeat rate or respiration rate of a human target, with a radar-based system is a complex endeavor. For example, the amplitude of the heartbeat signal is generally smaller than the amplitude of the respiration signal of the human target. The amplitude of the heartbeat signal is also generally smaller than the amplitude caused by the movement of the human target (e.g., when walking), as well as RBM of the human target (e.g., such as lifting an arm, twisting the torso, shaking of the legs, etc.). Additionally, the signal shape of a single heartbeat may be dependent on the subject, the chosen measurement spot, and the distance to the antenna.

Figure 2:
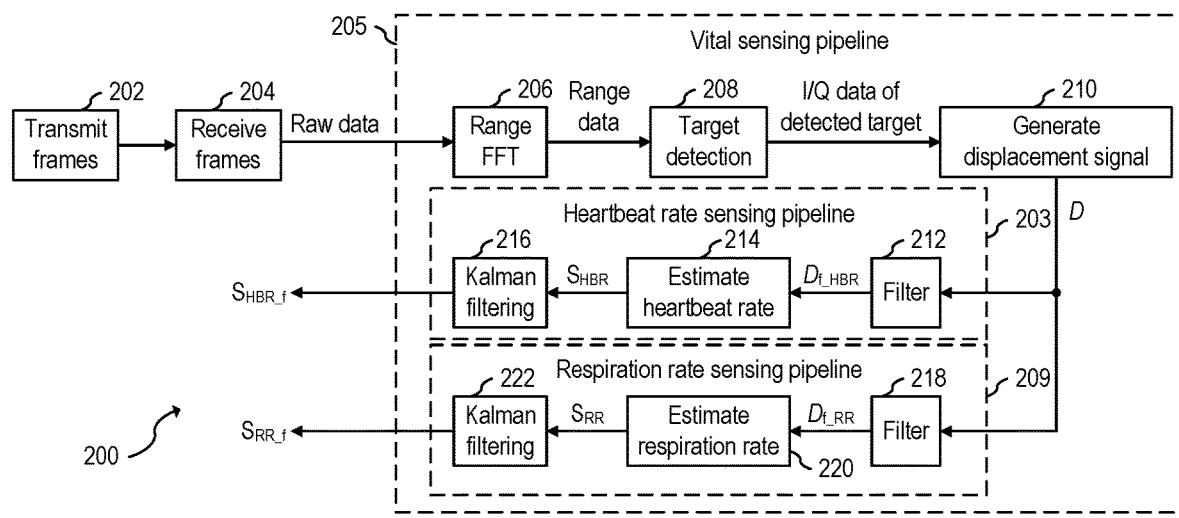
FIGS. 2 and 3 show flow charts of embodiment methods for estimating heartbeat rate and respiration rate of a human target, according to an embodiment of the present invention.

FIG. 2 shows a flow chart of embodiment method 200 for estimating heartbeat rate and respiration rate of a human target, according to an embodiment of the present invention. Radar system 100 may implement method 200. For example, in some embodiments, steps 202 and 204 may be performed by millimeter-wave radar sensor 102 and step 205 (which includes steps 206, 208, 210, 212, 214, 216, 218, 220, and 222) may be performed by processing system 104.

During step 202, millimeter-wave radar 102 sensor transmits, e.g., linear chirps organized in frames using transmitter (TX) circuit 120. The time between chirps of a frame is generally referred to as pulse repetition time (PRT). In some embodiments, the time interval between the end of the last chirp of a frame and the start of the first chirp of the next frame is the same as the PRT so that all chirps are transmitted (and received) equidistantly.

In some embodiments, the chirps have a bandwidth of 2 GHz within the 60 GHz UWB band, the frame time has a duration of 1.28 s, and the PRT is 5 ms (corresponding to an effective sampling rate of 200 Hz). Other values may also be used.

After reflection from objects in scene 108, receiver (RX) circuit 122 receives reflected radar signals during step 204. During step 204, raw digital data (also referred to as raw data or radar data) are generated based on the reflected radar signals received by millimeter-wave radar 102. For example, in some embodiments, during step 204, the transmitted and received radar signals are mixed to generate an intermediate frequency (IF) signal. The IF signal may be referred to as the beat signal. The IF signal is then filtered (e.g., with a low-pass and/or band-pass filter) and digitized with an analog-to-digital converter (ADC) to generate the raw data.

During step 205, one or more vital signs (e.g., $S_{HBR\_f}$, $S_{RR\_f}$) of a single human target are estimated based on the raw data. For example, in some embodiments, steps 206, 208 and 210 are performed to generate a target displacement signal D based on the raw data. The target displacement signal D is then filtered (e.g., during steps 212 and/or 218) to generate a vital sign filtered displacement signal (e.g., $D_{f\_HBR}$, $D_{f\_RR}$). An estimate of the vital sign (e.g., $S_{HBR}$, $S_{RR}$) is then generated based on the vital sign filtered displacement signal (e.g., during steps 214 and/or 220). A filtered vital sign (e.g., $S_{HBR\_f}$, $S_{RR\_f}$) is then generated based on the estimated vital sign of the human target.

For example, during step 206, a range fast Fourier transform (FFT) is performed on the raw data to generate range data. For example, in some embodiments, the raw data are zero-padded and the FFT is applied to generate the range data, which may include range information of a plurality of targets.

In some embodiments, the range FFT is applied on all samples of the observation window. The observation window may be implemented as consecutive windows or as sliding windows and may have a length of one or more frames. For example, in some embodiments, the observation window is implemented as a sliding window in which the length of the observation window corresponds to a plurality of time steps that are evaluated during each time step. For example, in an embodiment in which the time step is equal to 1 frame, and the observation window is a sliding window with 8 frames, then, for each frame, the last 8 frames are used as the observation window. In an embodiment, an observation window with a duration of 8 frames has a duration of about 10 s. In some embodiments, each frame includes only a single chirp and the observation window includes 1 chirp. In some embodiments, the observation window is not limited to frames and may include any number of chirps.

In some embodiments, range data, such as a range image, such as a range-Doppler image (RDI) or a range-angle image (RAI) is generated during step 206.

During step 208, detection of potential targets is performed. For example, in some embodiments, potential targets are identified by comparing power levels of the range image with a threshold, where points above the threshold are labeled as targets while points below the threshold are labeled as non-targets. In some embodiments, the range of interest associated with the detected target (the target distance or target bin) is identified based on the location of peaks of the range image having power levels above the threshold.

In some embodiments, an order statistics (OS) constant false alarm rate (CFAR) (OS-CFAR) detector is performed during step to identify potential targets.

In some embodiments, target range bins are clustered to "fuse" the target point cloud belonging to one target to a single target and thus determine the mean range of such single target. For example, in an embodiment, a density-based spatial clustering of applications with noise (DBSCAN) algorithm is used to associate targets to clusters. Other clustering algorithms may also be used. In some embodiments, the clustered targets are used to identify the range of interest associated with the detected target (the target distance or target bin).

The output of step 208 is target I/Q data associated with detected targets.

During step 210, a target displacement signal D is generated for each detected target based on the respective I/Q data, where the displacement signal D is indicative of the movement of the respective detected target. As will be described in more detail below, in some embodiments, moving targets, and targets exhibiting RBM or IMP may be ignored (e.g., the displacement signal D for such targets may not be generated or may not be further processed, and/or an estimated respiration rate $S_{RR}$ and estimated heartbeat rate $S_{HBR}$ may not be generated).

In some embodiments, a single displacement signal D associated with a single target is generated during step 210. In some embodiments in which multiple targets are detected, a single displacement signal D is generated, where the single displacement signal is associated with the target exhibiting the highest power (e.g., in the radar image).

During step 212, filtering is performed on the displacement signal D to generate a heartbeat filtered displacement signal $D_{f\_HBR}$ (e.g., of the single target). As will be described in more detail below, in some embodiments, the step of filtering 212 includes performing wavelet denoising and sinc filtering on the displacement signal D to generate the filtered displacement signal $D_{f\_HBR}$. The corner frequencies used during step 212 may be designed/selected to extract heartbeat rate information. For example, in some embodiments, the filtering performed during step 212 may be designed to extract information in the 0.5 Hz to 3.5 Hz, for example. Other ranges are also possible.

During step 214, the heartbeat rate $S_{HBR}$ (e.g., of the single target) is estimated based on the filtered displacement signal $D_{f\_HBR}$. As will be described in more detail below, in some embodiments, estimating the heartbeat rate may involve performing an FFT or counting peaks of the filtered displacement signal $D_{f\_HBR}$.

During step 216, Kalman filtering is performed on the estimated heartbeat rate $S_{HBR}$ to generate a final heartbeat rate estimate $S_{HBR\_f}$.

As illustrated in FIG. 2, steps 212, 214 and 216 are part of heartbeat rate sensing pipeline 203. As also illustrated in FIG. 2, a similar pipeline (e.g., 209) may be used for sensing other vital signs, such as respiration rate. For example, during step 218, filtering is performed on the displacement signal D to generate a respiration filtered displacement signal $D_{f\_RR}$ (e.g., of the single target). In some embodiments, steps 218 may be performed in a similar manner as step 212, except with corner frequencies designed/selected to extract respiration rate information. For example, in some embodiments, the filtering performed during step 218 may be designed to extract information in the 0.1 Hz to 0.4 Hz, for example. Other ranges are also possible.

During step 220, the respiration rate $S_{RR}$ (e.g., of the single target) is estimated based on the filtered displacement signal $D_{f\_RR}$. In some embodiments, steps 220 may be performed in a similar manner as step 214.

During step 222, Kalman filtering is performed on the estimated respiration rate $S_{RR}$ to generate a final respiration rate estimate $S_{RR\_f}$.

In some embodiments, the Kalman filters used during steps 216 and 220 may be implemented in any way known in the art.

In some embodiments, performing Kalman filtering on the heartbeat rate $S_{HBR}$ and respiration rate $S_{RR}$ advantageously results in a smoother final heartbeat rate estimate $S_{HBR\_f}$ and respiration rate estimate $S_{RR\_f}$, respectively.

In some embodiments, steps 216 and/or 222 may be omitted. For example, in some embodiments, step 222 may be omitted to save on computational costs (so that $S_{RR\_f}$ is equal to $S_{RR}$) while step 216 may be performed to improve the accuracy of the heartbeat rate estimate. Other implementations are also possible.

In some embodiments, the estimated heartbeat rate $S_{HBR\_f}$ and estimated respiration rate $S_{RR\_f}$ are displayed, e.g., in a screen of a mobile phone or computer. In some embodiments, the estimated heartbeat rate $S_{HBR\_f}$ and estimated respiration rate $S_{RR\_f}$ are transmitted to an external user (e.g., a remote server) for further processing and/or storage. In some embodiments, the estimated heartbeat rate $S_{HBR\_f}$ and estimated respiration rate $S_{RR\_f}$ are stored in volatile or non-volatile memory (e.g., of a mobile device, computer or remote server), e.g., for later retrieval and/or further processing. Other uses of the estimated heartbeat rate $S_{HBR\_f}$ and estimated respiration rate $S_{RR\_f}$ are also possible. For example, in some embodiments, the estimated heartbeat rate $S_{HBR\_f}$ and estimated respiration rate $S_{RR\_f}$ are used for sleep monitoring and analysis, such as for identifying and predicting sleep patterns over a time window.

In some embodiments, the accuracy of the estimated vital sign(s) (e.g., heartbeat rate or respiration rate) of a single human target may be affected by the number of human targets present in scene 108. For example, when more than 1 human target is present in scene 108, the quality/accuracy of the estimated vital sign(s) for the single human target may be (e.g., substantially) degraded.

Figure 3:
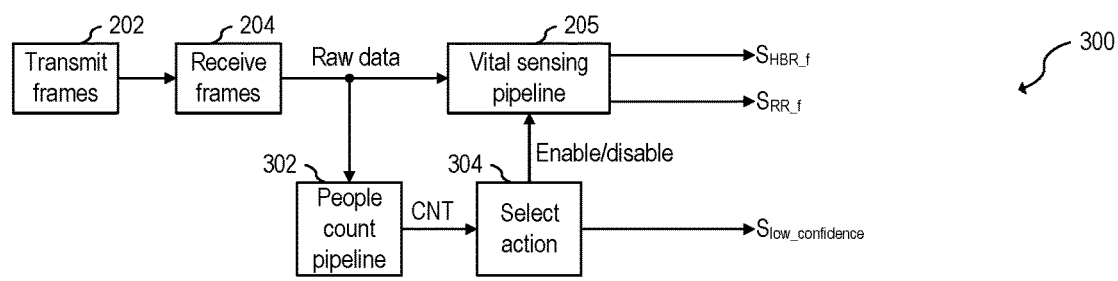

In some embodiments, the number of human targets present in scene 108 is counted, and such count is used to enable/disable the vital sensing pipeline (e.g., for performing step 205) and/or to produce an indication of the confidence level of the vital sign estimate(s) (e.g., $S_{HBR\_f}$ and $S_{RR\_f}$). For example, FIG. 3 shows a flow chart of embodiment method 300 for estimating heartbeat rate and respiration rate of a single human target, according to an embodiment of the present invention. Method 300 includes steps 202, 204, 205, 302 and 304. Steps 202, 204 and 205 may be performed in a similar manner as described with respect to method 200. In some embodiments, processing system 104 performs steps 302 and 304.

During step 302, the number of people CNT in scene 108 is counted. For example, in some embodiments, the number of people CNT in scene 108 is counted in a conventional manner.

During step 304, an action is decided based on the number of people CNT in scene 108. For example, in some embodiments, the vital sign estimation step 205 may be performed or not performed based on the number of people CNT present in scene 108. For example, in some embodiments, if the number of people CNT is zero, then the vital sign estimation step 205 is not performed (e.g., the vital sensing pipeline for estimating vital signs of the single human target is disabled during step 304). By not estimating vital signs when no human target is detected in scene 108, some embodiments advantageous achieve lower power consumption and/or avoid displaying erroneous vital sign estimates.

In some embodiments, if the number of people CNT is greater than 1 (e.g., 2, 3, or more), a low confidence signal $S_{low\_confidence}$ may be asserted (activated) during step 304 to indicate that the vital estimates (e.g., $S_{HBR\_f}$, $S_{RR\_f}$) of the single human target may be inaccurate (e.g., since the presence of a one or more additional human targets in scene 108 may interfere with the vital sign estimates). In some embodiments, if the number of people CNT is greater than 1, then the vital signal estimation step 205 is not performed (e.g., the vital sensing pipeline for estimating vital signs of the single human target is disabled during step 304).

In some embodiments, if the number of people CNT is equal to 1, step 205 is performed (e.g., vital sensing pipeline is/remains enabled during step 304 so that vital sign estimates (e.g., $S_{HBR\_f}$, $S_{RR\_f}$) are generated during step 205), and the low confidence signal $S_{low\_confidence}$ may be deasserted (deactivated) during step 304 to indicate that the vital estimates (e.g., $S_{HBR\_f}$, $S_{RR\_f}$) of the single human target are not degraded by the presence of additional human targets in scene 108.

Figure 4:
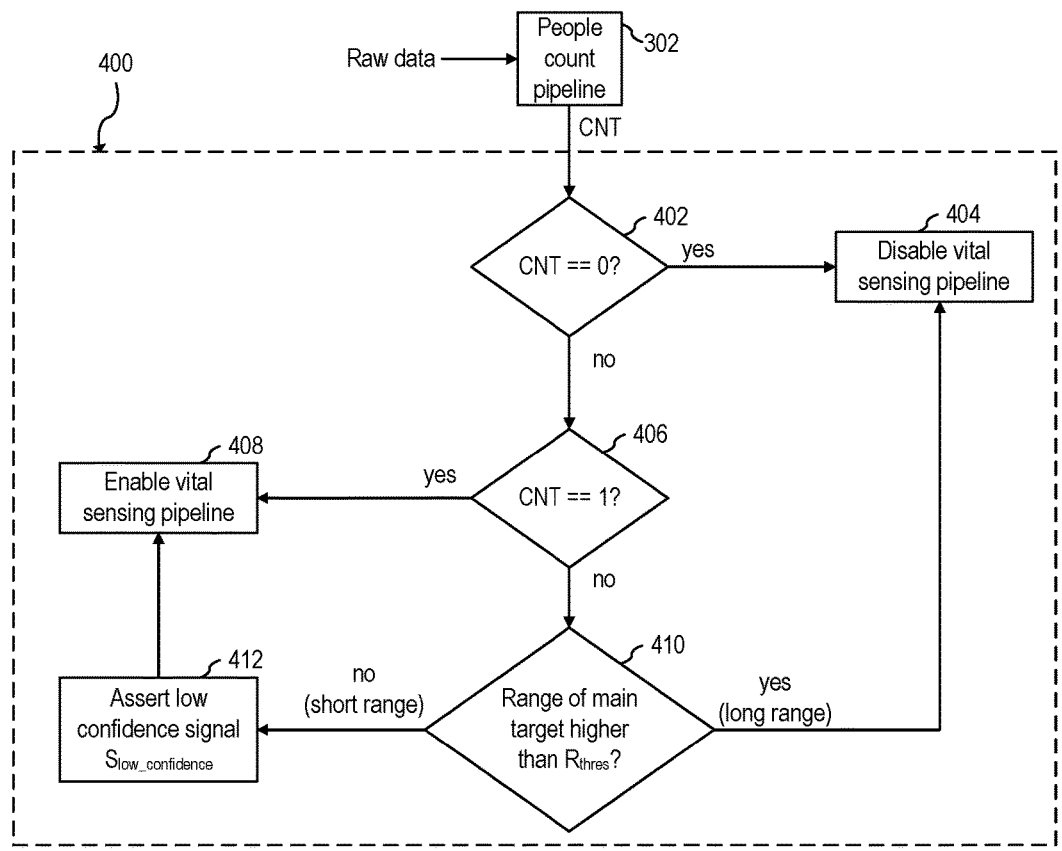
FIG. 4 shows a flow chart of an embodiment method for performing vital sensing on a single human target based on the number of human targets in a field-of-view (FoV) of the millimeter-wave radar sensor of FIG. 1, according to an embodiment of the present invention.

FIG. 4 shows a flow chart of embodiment method 400 for performing vital sensing on a single human target based on the number of human targets in a field-of-view (FoV) of millimeter-wave radar sensor 102, according to an embodiment of the present invention. Step 304 may be implemented as method 400.

During step 402, the number of people CNT in scene 108 (e.g., in the FoV of millimeter-wave radar sensor 102) is received. If the number of people CNT is zero (i.e., no human target is detected in scene 108), then the vital sensing pipeline (e.g., 205) is disabled during step 404.

If it is determined during step 402 than there is at least one human target in scene 108 (output "no" from step 402), then if CNT is equal to 1 (i.e., if there is only one human target detected in scene 108), then the vital sensing pipeline is enabled or kept enabled during step 408 so that vital signs are estimated (e.g., during step 205).

If it is determined during step 406 that there is more than one human target in scene 108 (output "no" from step 406), then the range of the main target (e.g., the target associated with the vital sign estimates performed or to be performed during step 205, such as the human target associated with displacement signal D) is compared with a predetermined threshold $R_{thres}$. If the main target is farther than the predetermined threshold $R_{thres}$, then the vital sensing pipeline is disabled during step 404. If the main target is closer than the predetermined threshold $R_{thres}$, then the low confidence signal $S_{low\_confidence}$ is asserted during step 412, and the vital sensing pipeline is or is kept enabled during step 404.

In some embodiments, the accuracy of vital sign estimates of a main target in a multitarget scene is higher in short range settings (output "no" from step 410) than in long range settings (output "yes" from step 410). Thus, in some embodiments, by disabling the vital sensing pipeline in a multi-target long range vital sensing setting, some embodiments advantageously save power and computational costs and avoid determining and/or providing vital sign estimates with low accuracy. In some embodiments, by providing vital signs of the main target in a multi-target short range vital sensing settings while asserting the low confidence signal, some embodiments advantageously provide estimates of the vital signs of the main target while indicating that the confidence in such estimates is low.

Examples of short range settings include: a human target in front of a laptop at a distance lower than $R_{thres}$ (where the laptop includes millimeter-wave radar sensor 102), a human target driving a car at a distance lower than $R_{thres}$ from the millimeter-wave radar sensor 102 (which may be located, e.g., in a steering wheel or dashboard of a car), and a human target sleeping next to a mobile phone at a distance lower than $R_{thres}$ (where the mobile phone includes millimeter-wave radar sensor 102). Examples of long range settings include: a human target sitting in a sofa in front of a television at a distance higher than $R_{thres}$ (where the television includes millimeter-wave radar sensor 102), and a human target located (e.g., sitting, standing) at a distance higher than $R_{thres}$ from a security camera (where the security camera includes millimeter-wave radar sensor 102).

In some embodiments, $R_{thres}$ may be, e.g., about 1.2 meters. Other values (e.g., higher than 1.2 meters, such as 1.5 meters or higher, or lower than 1.2 meters, such as 1 meter, or lower) may also be used.

Figure 5:
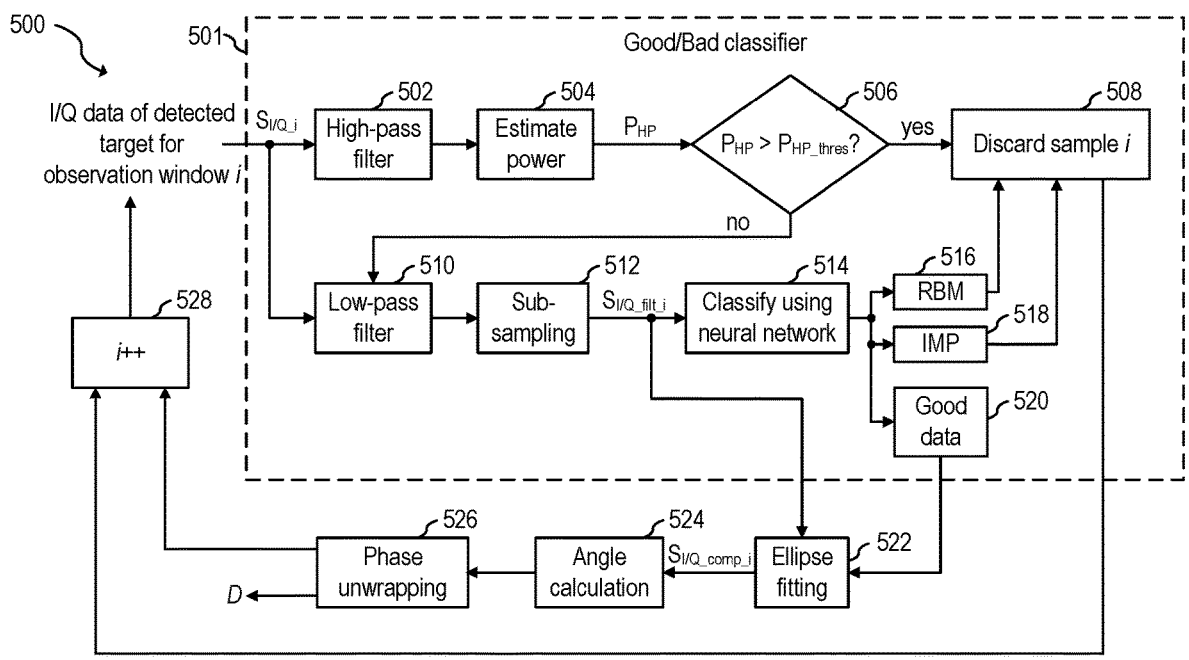
FIG. 5 shows a flow chart of an embodiment method for generating a displacement signal, according to an embodiment of the present invention.

FIG. 5 shows a flow chart of embodiment method 500 for generating a displacement signal, according to an embodiment of the present invention. Step 210 may be performed as method 500.

During step 502, target I/Q data $S_{I/Q\_i}$ associated with observation windows i for a (e.g., single) detected target is high-passed filtered. In some embodiments, the observation window covers one or more frames. In some embodiments, a corner frequency of the high-pass filter used during step 502 is 20 Hz. Other frequencies, such as higher than 20 Hz (e.g., 23 Hz, Hz or higher), or lower than 20 Hz (e.g., 18 Hz, 10 Hz, or lower) may also be used.

During step 504, the power associated with target I/Q data $S_{I/Q\_i}$ is estimated, e.g., in a known manner, to generate power estimate $P_{HP}$. If power estimate $P_{HP}$ is higher than a predetermined threshold $P_{HP\_thres}$ (output "yes" from step 506), then the target I/Q data $S_{I/Q\_i}$ is discarded during step 508, and the next observation window is processed (as shown by step 528). By discarding target I/Q data associated with high power at high frequencies (e.g., high power at frequencies higher than the corner frequency of the high-pass filter used during step 502), some embodiments advantageously discard and avoid processing target I/Q data that may be unsuitable for extracting vital signs. For example, in some embodiments, performing vital sign estimation involves estimating micro-Doppler signals below, e.g., 5 Hz. Movement of the human target, such as walking or running, may prevent the extraction of accurate vital signs (e.g., $S_{HBR\_f}$, $S_{RR\_f}$) of a detected human target. Thus, in some embodiments, the high-frequency power $P_{HP}$ serves as an indication of the amount of movement of the human target during observation window i. Thus, by discarding samples associated with high power at high frequencies, some embodiments advantageously avoid processing target I/Q data that may be unsuitable for estimating accurate vital signs (e.g., $S_{HBR\_f}$, $S_{RR\_f}$).

If power estimate $P_{HP}$ is not higher than a predetermined threshold $P_{HP\_thres}$ (output "no" from step 506), then the target I/Q data $S_{I/Q\_i}$ is further processed during step 510. During steps 510 and 512, target I/Q data $S_{I/Q\_i}$ is low-pass filtered and down-sampled to generate filtered I/Q data $S_{I/Q\_filt\_i}$. By low-pass filtering the target I/Q data $S_{I/Q\_i}$, some embodiments advantageously remove high frequency noise, which may aid in improving the accuracy of the vital sign estimates (e.g., $S_{HBR\_f}$, $S_{RR\_f}$).

In some embodiments, a corner frequency of the low-pass filter used during step 510 may be 20 Hz. Other frequencies, such as higher than 20 Hz (e.g., 23 Hz, 25 Hz or higher), or lower than 20 Hz (e.g., 18 Hz, 10 Hz, or lower) may also be used.

In some embodiments, the corner frequency of the low-pass filter used during step 510 may be equal to the corner frequency of the high-pass filter used during step 502. In some embodiments, the corner frequency of the low-pass filter used during step 510 and the high-pass filter used during step 502 may be different.

In some embodiments, using a corner frequency for the low-pass filter and high-pass filter at or around 20 Hz (e.g., between 15 Hz and 25 Hz) advantageously avoids filtering out information that may be useful in estimating vital signs while removing high frequency noise (e.g., related to large body movements). In some embodiments, any small body movement retained in filtered I/Q data $S_{I/Q\_filt\_i}$ may be addressed (e.g., compensated for), e.g., in steps 514 and 522.

Figure 6:
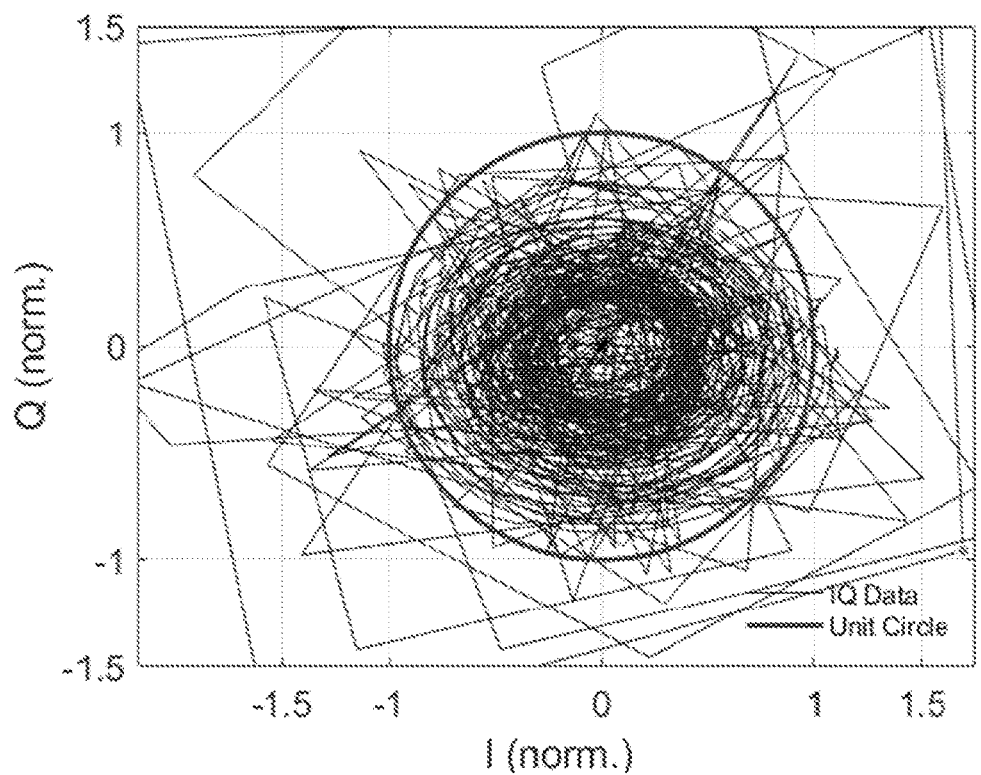
FIGS. 6 and 7 show exemplary in-phase (I) and quadrature (Q) plots of low quality I/Q data and high quality I/Q data, respectively.
Figure 7:
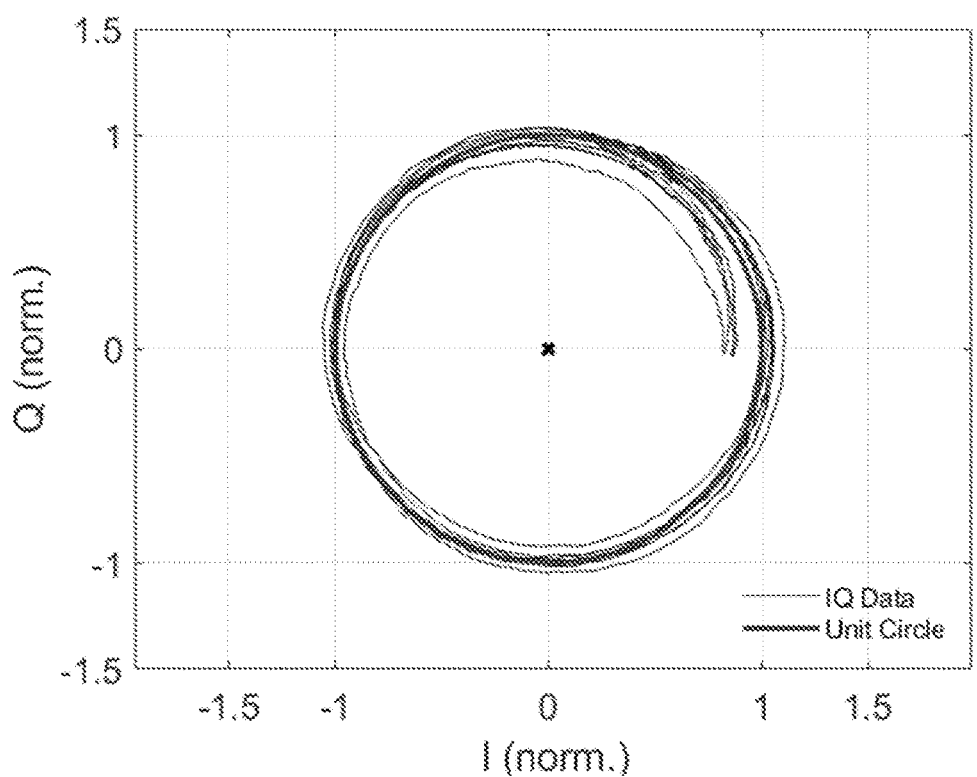

During step 514, the filtered I/Q data $S_{I/Q\_filt\_i}$ is classified using a neural network. For example, in some embodiments, a deep neural network (DNN) performs a multilevel classification to classify the filtered I/Q data $S_{I/Q\_filt\_i}$ into 3 classes: RBM (516), IMP (518), and Good Data (520). Classes RBM (516) and IMP (518) correspond to low quality data while class Good Data (520) corresponds to high quality data. Exemplary I-Q plots of low quality I/Q data and high quality I/Q data are shown in FIGS. 6 and 7, respectively.

In some embodiments, the neural network used during step 514 may be implemented as a SincNet plus CNN layers in a known manner. Other implementations are also possible.

In some embodiments, the neural network (e.g., SincNet plus CNN layers) used during step 514 may be trained in a known manner, e.g., using supervised training.

As shown in FIG. 5, filtered I/Q data $S_{I/Q\_filt\_i}$ classified as RBM or IMP is discarded during step 508 (and is not further processed), and the next observation window is processed (as shown by step 528). By discarding filtered I/Q data $S_{I/Q\_filt\_i}$ classified as RBM or IMP, some embodiments advantageously discard and avoid processing I/Q data that may be unsuitable for extracting vital signs.

If the filtered I/Q data $S_{I/Q\_filt\_i}$ is classified during step 514 as Good Data (520), then ellipse fitting is performed in a known manner on the filtered I/Q data $S_{I/Q\_filt\_i}$ during step 522 to generate compensated I/Q data $S_{I/Q\_comp\_i}$. For example, during step 522, a conventional ellipse fitting algorithm (also referred to as ellipse correction algorithm) is applied to the I-Q trace (of the complex range data) associated with the detected target to compensate for offset, amplitude, and gain errors. In some embodiments, the compensated I/Q data $S_{I/Q\_comp\_i}$ are I-Q signals that correspond to the best fit ellipse associated with the filtered I/Q data $S_{I/Q\_filt\_i}$. Some embodiments may avoid using the ellipse fitting algorithm. For example, some embodiments may use an offset compensation algorithm during step 522 or may avoid implementing step 522. In some embodiments, a neural network may be used for generating the compensated I/Q data $S_{I/Q\_comp\_i}$ based on the filtered I/Q data $S_{I/Q\_filt\_i}$. Other implementations are also possible.

During step 524, the angle of the compensated I/Q data $S_{I/Q\_comp\_i}$ is calculated by arctangent demodulation of the I-Q signals from the selected range bin selected during step 208 (the I-Q signals associated with the detected target). The resulting phase values in the range of $[-\pi,+\pi]$ are unwrapped between two consecutive data points during step 526. For example, during step 526, the phase is unwrapped by adding or subtracting $2\pi$ for phase jumps larger than $-\pi$ or $+\pi$, respectively, to keep the phase between $-\pi$ or $+\pi$.

In some embodiments, steps 524 and 526 may be performed by calculating the displacement signal D as $$D = \frac{\lambda}{4\pi} \cdot \text{unwrap}\left(\arctan\frac{Q}{I}\right) \quad (1)$$

where D represents the time-domain displacement signal, $\lambda$ is the wavelength of the carrier frequency of the chirps (e.g., transmitted during step 202), $\lambda/2$ represents the unambiguousness (phase) range, and I and Q are the in-phase and quadrature-phase components of the carrier, respectively, associated with the detected target.

As shown in FIG. 5, in some embodiments, once the displacement signal D is determined for an observation window i, the next observation window i++ is processed.

In some embodiments, a module performing the steps 502, 504, 506, 508, 510, 512, 514, 516, 618, and 520, is referred to as a Good/Bad classifier 501. As illustrated in FIG. 5, the Good/Bad classifier 501 provides filtered I/Q data to be processed during step 522 containing I/Q data classified as good data (520) while not providing I/Q data classified as RBM (516) or IMP (518) as well as not providing I/Q data of human target exhibiting large movements (e.g., step 506, output "yes").

Figure 8:
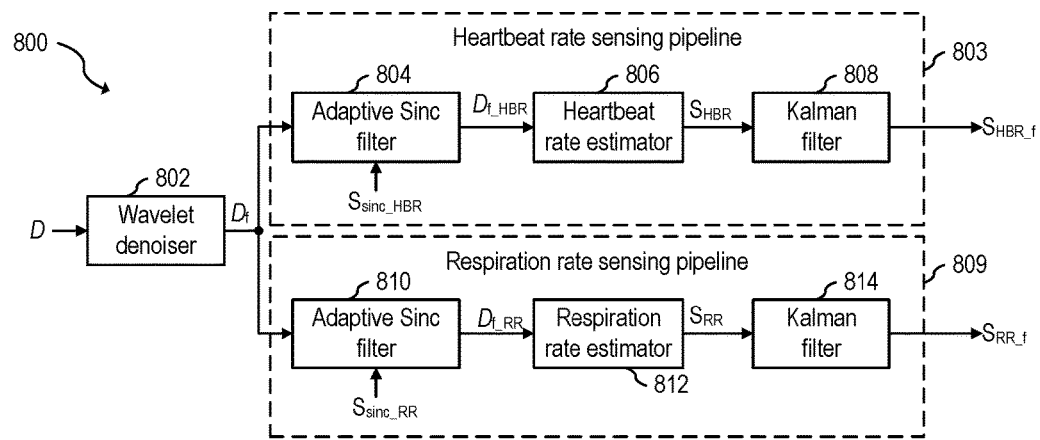
FIG. 8 shows a block diagram of an embodiment for estimating heartbeat rate and respiration rate of a single human target from the displacement signal of FIG. 5, according to an embodiment of the present invention.

FIG. 8 shows a block diagram of embodiment module 800 for estimating heartbeat rate and respiration rate of a single human target from target displacement signal D, according to an embodiment of the present invention. Module 800 includes wavelet denoiser 802, heartbeat rate sensing pipeline 803 and respiration rate sensing pipeline 809. Heartbeat rate sensing pipeline 803 includes adaptive Sinc filter 804, heartbeat rate estimator 806 and Kalman filter 808. Respiration rate sensing pipeline 809 includes adaptive Sinc filter 810, respiration rate estimator 812 and Kalman filter 814. Processing system 104 may implement module 800. Heartbeat rate sensing pipeline 203 may be implemented as heartbeat rate sensing pipeline 803. Respiration rate sensing pipeline 209 may be implemented as respiration rate sensing pipeline 809.

As shown in FIG. 8, wavelet denoiser 802 receives target displacement signal D (e.g., from step 526) and generates denoised displacement signal $D_f$. For example, in some embodiments, wavelet denoiser 802 performs a wavelet transform on target displacement signal D in a known manner, removes wavelet coefficients that fall below a threshold, and then perform an inverse wavelet transform on the resulting coefficients to generate the denoised displacement signal $D_f$.

As shown in FIG. 8, adaptive Sinc filter 804 receives denoised displacement signal $D_f$ and generates heartbeat filtered displacement signal $D_{f\_HBR}$, where the settings of the adaptive Sinc filter are based on one or more selection signals $S_{sinc\_HBR}$. As will be described in more detail below, selection signal(s) $S_{sinc\_HBR}$ may come from Kalman filter 808, may be based on signal $S_{RR}$, or may be generated by another block, such as a prediction block.

In some embodiments, adaptive Sinc filter 804 is configured to change the filter settings (e.g., change the corner frequencies of the Sinc filters) to facilitate estimation of the heartbeat rate by heartbeat rate estimator 806.

Figure 9:
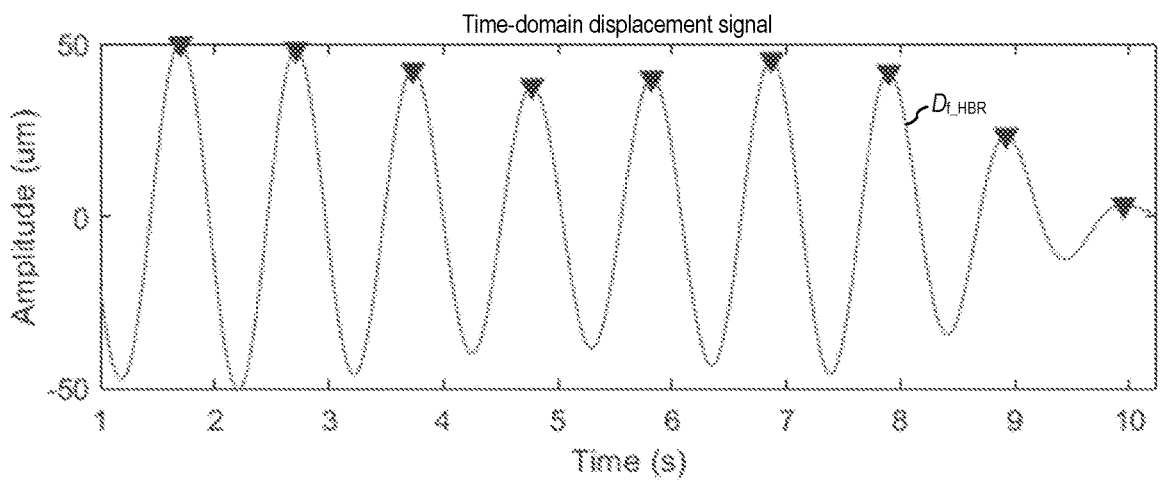
FIG. 9 shows an exemplary displacement signal, and identified peaks for estimating a heartbeat rate, according to an embodiment of the present invention.

Heartbeat rate estimator 806 is configured to estimate the heartbeat rate $S_{HBR}$ from heartbeat filtered displacement signal $D_{f\_HBR}$. In some embodiments, heartbeat rate estimator 806 estimates the heartbeat rate $S_{HBR}$ by counting the number of peaks in heartbeat filtered displacement signal $D_{f\_HBR}$ and estimating the heartbeat rate $S_{HBR}$ based on the number of detected peaks per unit of time. For example, FIG. 9 shows an exemplary displacement signal $D_{f\_HBR}$, and identified peaks for estimating heartbeat rate $S_{HBR}$, according to an embodiment of the present invention. In some embodiments, heartbeat rate estimator 806 estimates the heartbeat rate $S_{HBR}$ by performing an FFT on displacement signal $D_{f\_HBR}$ and detecting the highest peak of the FFT (where the heartbeat rate $S_{HBR}$ is estimated as the frequency corresponding to the location of the peak of the FFT). Other implementations of heartbeat rate estimator 806, such as based on measuring the time between peaks in heartbeat filtered displacement signal $D_{f\_HBR}$, is also possible.

Kalman filter 808 is configured to provide a prediction of the heartbeat rate $S_{HBR\_f}$ based on the history of previous heartbeat rates and on the current estimated heartbeat rate $S_{HBR}$. In some embodiments, Kalman filter 808 advantageously smoothens the heartbeat rate estimation. Kalman filter 808 may be implemented in any way known in the art.

In some embodiments, modules 810, 812, and 814 may be implemented in an analogous manner as modules 804, 806, and 808, but targeting the respiration rate as opposed to the heartbeat rate. For example, the corner frequencies of adaptive Sinc filter 810 for generating respiration filtered displacement signal $D_{f\_RR}$ may be different (e.g., lower) than the corner frequencies of adaptive Sinc filter 810.

As shown in FIG. 8, in some embodiments, steps 212 and 218 may be implemented with Sinc filters 804 and 810, respectively, and with a shared wavelet denoiser 802.

In some embodiments, one or more modules 804, 808, 810, and 814 may be omitted. In some embodiments, only heartbeat rate is estimated (and modules 810, 812, and 814) may be omitted. In some embodiments, only respiration rate is estimated (and modules 804, 806, and 808 may be omitted). Other implementations are also possible.

Figure 10:
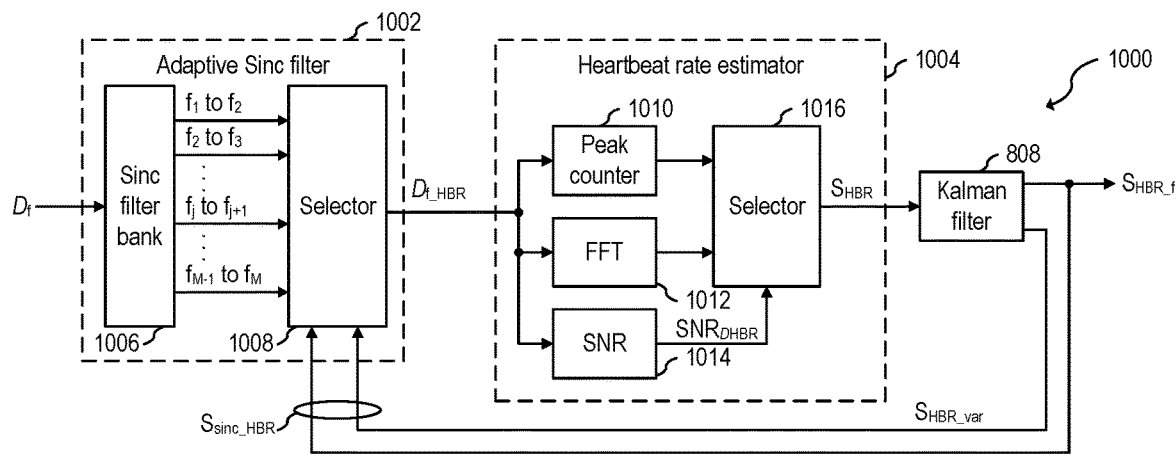
FIG. 10 shows a block diagram of a heartbeat rate sensing pipeline, according to an embodiment of the present invention.

FIG. 10 shows a block diagram of heartbeat rate sensing pipeline 1000, according to an embodiment of the present invention. Heartbeat rate sensing pipeline 1000 includes adaptive Sinc filter 1002, heartbeat rate estimator 1004, and Kalman filter 808. Adaptive Sinc filter 1002 includes Sinc filter bank 1006 and selector 1008. Heartbeat rate estimator 1004 includes peak counter 1010, FFT module 1012, SNR determination module 1014, and selector 1016. Heartbeat rate sensing pipeline 803 may be implemented as heartbeat rate sensing pipeline 1000. Adaptive Sinc filter 804 may be implemented as adaptive Sinc filter 1002. Heartbeat rate estimator 806 may be implemented as heartbeat rate estimator 1004.

In some embodiments, peak counter 1010 is configured to count peaks in a displacement signal (e.g., $D_{f\_HBR}$), e.g., as illustrated in FIG. 9, and extract a frequency (e.g., in beats per minute) based on the number of peaks detected per unit time. In some embodiments, peak counter 1010 may be implemented in any way known in the art.

In some embodiments, FFT module 1012 is configured to perform an FFT on a displacement signal (e.g., $D_{f\_HBR}$) to generate a frequency spectrum and extract a frequency (e.g., in beats per minute) based on the location of a (e.g., highest) peak in the frequency spectrum. In some embodiments, FFT module 1012 may be implemented in any way known in the art.

In some embodiments, SNR module 1014 is configured to extract the SNR of a displacement signal (e.g., $D_{f\_HBR}$). SNR module 1014 may be implemented in any way known in the art.

Sinc filter bank 1006 is configured to receive denoised displacement signal $D_f$ (e.g., from wavelet denoiser 802) and apply M Sinc filters to denoised displacement signal $D_f$ to generate M corresponding outputs. In some embodiments, the corner frequencies of each of the M Sinc filters of Sinc filter bank 1006 are fixed.

In some embodiments, the bandwidth of each Sinc filter of Sinc filter bank 1006 is the same. For example, in some embodiments, the bandwidth of each Sinc filter of Sinc filter bank 1006 is 0.1 Hz, $f_1$ is 0.7 Hz, and $f_M$ is 3 Hz (so that M is 24). Other values for $f_1$, $f_M$, and the bandwidth of each Sinc filter of Sinc filter bank 1006 may also be used. For example, in some embodiments, the bandwidth of each Sinc filter of Sinc filter bank 1006 may be higher than 0.1 Hz (e.g., 0.15 Hz, 0.2 Hz, or higher) or lower than 0.1 Hz (e.g., 0.08 Hz, 0.05 Hz, or lower). In some embodiments, corner frequency $f_1$ may be lower than 0.7 Hz (e.g., 0.65 Hz, 0.6 Hz or lower), or higher than 0.7 Hz (e.g., 0.8 Hz, 0.9 Hz or higher). In some embodiments, corner frequency $f_M$ may be lower than 3 Hz (e.g., 2.9 Hz, 2.7 Hz or lower), or higher than 3 Hz (3.2 Hz, 3.5 Hz or higher). In some embodiments, M may be lower than 24 (e.g., 20, 16, 12, 8, or lower), or higher than 24 (e.g., 28, 32, or higher). In some embodiments, M may be greater than 1.

In some embodiments, the bandwidth of each Sinc filter of Sinc filter bank 1006 may be different (e.g., broader or more granular).

Selector module 1008 is configured to select one or more outputs from the M outputs of Sinc filter bank 1006 based on final heartbeat rate estimate $S_{HBR\_f}$ and heartbeat rate variance $S_{HBR\_var}$ (where variance $S_{HBR\_var}$ represents the variance of the (e.g., recent) history of final heartbeat rate estimates $S_{HBR\_f}$) and produce displacement signal $D_{f\_HBR}$, where displacement signal $D_{f\_HBR}$ is formed by concatenating each of the selected outputs of Sinc filter bank 1006. For example, when the variance $S_{HBR\_var}$ is very low (e.g., a person with a stable heartbeat rate, such as varying less than 2 bpm across a relatively long time window, such as 1 minute, e.g., near the heartbeat rate initialization value of Kalman filter 216), selector 1008 may select a single output of Sinc filter bank 1006 based on the final heartbeat rate estimate $S_{HBR\_f}$. For example, in an embodiment in which each Sinc filter of Sinc filter bank 1006 has the same bandwidth of 0.1 Hz, if final heartbeat rate estimate $S_{HBR\_f}$ is 80 bpm (1.33 Hz) and the variance $S_{HBR\_var}$ is very low, then selector 1008 selects the output of the Sinc filter from 1.3 Hz to 1.4 Hz as the displacement signal $D_{f\_HBR}$.

Some embodiments may, instead of using variance $S_{HBR\_var}$ for selecting the number of Sinc filters to select from Sinc filter bank 1006, use a fixed number of Sinc filters. For example, in some embodiments, if final heartbeat rate estimate $S_{HBR\_f}$ is 80 bpm (1.33 Hz), selector module 1008 may select two adjacent Sinc filters above (e.g., the Sinc filter from 1.3 Hz to 1.4 Hz and the Sinc filter from 1.4 Hz to 1.5 Hz) and three adjacent Sinc filters below (e.g., the Sinc filter from 1.2 Hz to 1.3 Hz. the Sinc filter from 1.1 Hz to 1.2 Hz, and the Sinc filter from 1 Hz to 1.1 Hz) irrespective of the value of variance $S_{HBR\_var}$.

In some embodiments, if the final heartbeat rate estimate $S_{HBR\_f}$ is at a boundary between two adjacent Sinc filters and the variance $S_{HBR\_var}$ is very low, then selector 1008 may select the two adjacent outputs and concatenate them to produce displacement signal $D_{f\_HBR}$. For example, in an embodiment in which each Sinc filter of Sinc filter bank 1006 has the same bandwidth of 0.1 Hz, if final heartbeat rate estimate $S_{HBR\_f}$ is 78 bpm (1.3 Hz) and the variance $S_{HBR\_var}$ is very low, then selector 1008 selects the output of the Sinc filter from 1.2 Hz to 1.3 Hz and the output of the Sinc filter from 1.3 Hz to 1.4 Hz, and concatenate both outputs to form the displacement signal $D_{f\_HBR}$.

In some embodiments, as the variance $S_{HBR\_var}$ increases, selector 1008 selects more outputs from Sinc filter bank 1006 (based on how high variance $S_{HBR\_var}$ is). When variance $S_{HBR\_var}$ is very high (e.g., when the heartbeat rate jumps from 80 bpm to 120 bpm in a relatively short time window, such as within 10 seconds), selector 1008 may select all M outputs of Sinc filter bank 1006 and concatenate them to form the displacement signal $D_{f\_HBR}$.

As shown in FIG. 10, heartbeat rate estimator 1004 may estimate heartbeat rate $S_{HBR}$ using peak counter 1010 or FFT 1012 based on the signal-to-noise ratio (SNR) of displacement signal $D_{f\_HBR}$. For example, in some embodiments, SNR module 1014 determines the SNR ($SNR_{DHBR}$) of displacement signal $D_{f\_HBR}$. If $SNR_{DHBR}$ is higher than a predetermined SNR threshold ($SNR_{thres}$), heartbeat rate estimator 1004 estimate heartbeat rate $S_{HBR}$ using an FFT (selector 1016 selects the output of FFT 1012 and provides it to Kalman filter 808). If $SNR_{DHBR}$ is lower than the predetermined SNR threshold ($SNR_{thres}$) heartbeat rate estimator 1004 estimate heartbeat rate $S_{HBR}$ by counting peaks of displacement signal $D_{f\_HBR}$ (selector 1016 selects the output of peak counter 1919 and provides it to Kalman filter 808).

A non-limiting example of a situation exhibiting a high SNR higher than SN threshold $SNR_{thres}$ in some embodiments is when a person sits in a very stable manner in front of the millimeter-wave radar sensor 102 in an otherwise empty room.

In some embodiments, during the beginning of normal operation (e.g., when the vital sensing pipeline used during step 205 is enabled), selector 1008 initially selects all M outputs of Sinc filter bank 1006. As Kalman filter 808 generates predictions for heartbeat rate $S_{HBR\_f}$ and variance $S_{HBR\_var}$ decreases, selector 1008 begins reducing the number of selected outputs from Sinc filter bank 1006.

In some embodiments, respiration rate sensing pipeline 809 may be implemented in an analogous manner as heartbeat rate sensing pipeline woo (e.g., with corner frequencies suitable for extracting respiration rate from a displacement signal).

Figure 11:
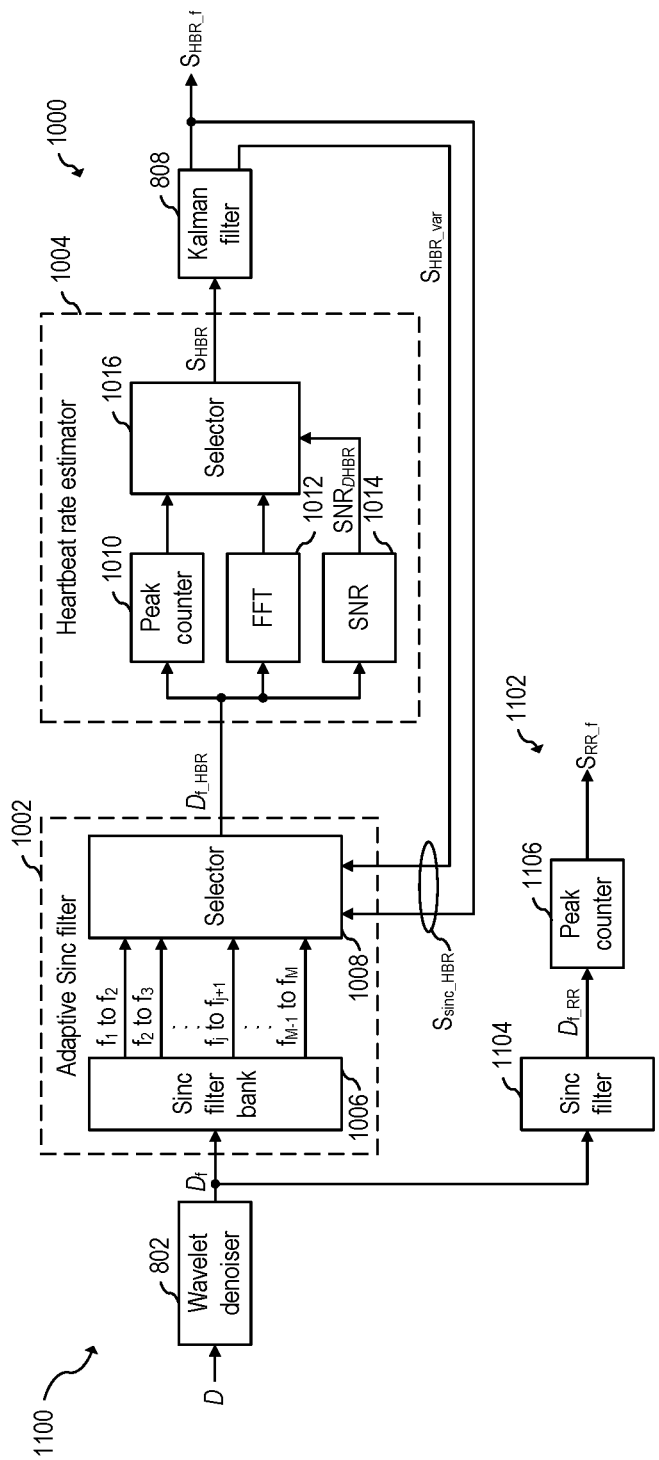
FIGS. 11-13 shows block diagram of embodiments for estimating heartbeat rate and respiration rate of a single human target from the displacement signal of FIG. 5, according to an embodiment of the present invention.

In some embodiments, the respiration rate of a human target is much more stable than the heartbeat rate of the human target. Thus, in some embodiments, the complexity of the respiration rate estimator may be lower than the complexity of the heartbeat rate estimator while maintaining comparable accuracy. For example, FIG. 11 shows a block diagram of embodiment module 1100 for estimating heartbeat rate and respiration rate of a single human target from displacement signal D, according to an embodiment of the present invention. Module 1100 includes heartbeat rate sensing pipeline 1000, respiration rate sensing pipeline 1102, and wavelet denoiser 802. Respiration rate sensing pipeline 809 may be implemented as respiration rate sensing pipeline 1102. Respiration rate estimator 812 may be implemented as peak counter 1106. Peak counter 1106 may be implemented in a similar manner as peak counter low. Processing system 104 may implement module 1100.

As shown in FIG. 11, in some embodiments, respiration rate sensing pipeline 1102 may be implemented with a Sinc filter 1104 for generating filtered displacement signal $D_{f\_RR}$, and peak counter 1106 for generating final respiration rate estimate $S_{RR\_f}$. In some embodiments, Sinc filter 1104 may be implemented with a low corner frequency $f_l$ equal to 0.2 Hz and a high corner frequency $f_h$ equal to 0.6 Hz. Other corner frequency values, such as with $f_l$ lower than 0.2 Hz (e.g., 0.15 Hz, 0.1 Hz, or lower) or higher than 0.2 Hz (e.g., 0.25 Hz or higher) and such as with $f_h$ lower than 0.6 Hz (e.g., 0.55 Hz, 0.5 Hz, or lower) or higher than 0.6 Hz (e.g., 0.65 Hz or higher).

The inventors realized that it is common for the respiration rate and the heartbeat rate to be correlated. For example, it is common for the heartbeat rate to be on the lower end of the heartbeat rate range when the respiration rate is on the lower end of the respiration rate range. Similarly, it is common for the heartbeat rate to be on the higher end of the heartbeat rate range when the respiration rate is on the higher end of the respiration rate range.

The inventors also realized that harmonics of the respiration rate (e.g., the third harmonics) may be in the range of a possible heartbeat rate and thus may interfere with heartbeat rate estimation. For example, the third harmonic of a respiration rate of 16 bpm is at 0.81 Hz. Thus, the third harmonics of a respiration rate of 16 bpm may result in additional peaks in the heartbeat displacement signal $D_{f\_HBR}$, which may cause an estimation of the heartbeat rate that is higher than the actual heartbeat rate.

Figure 12:
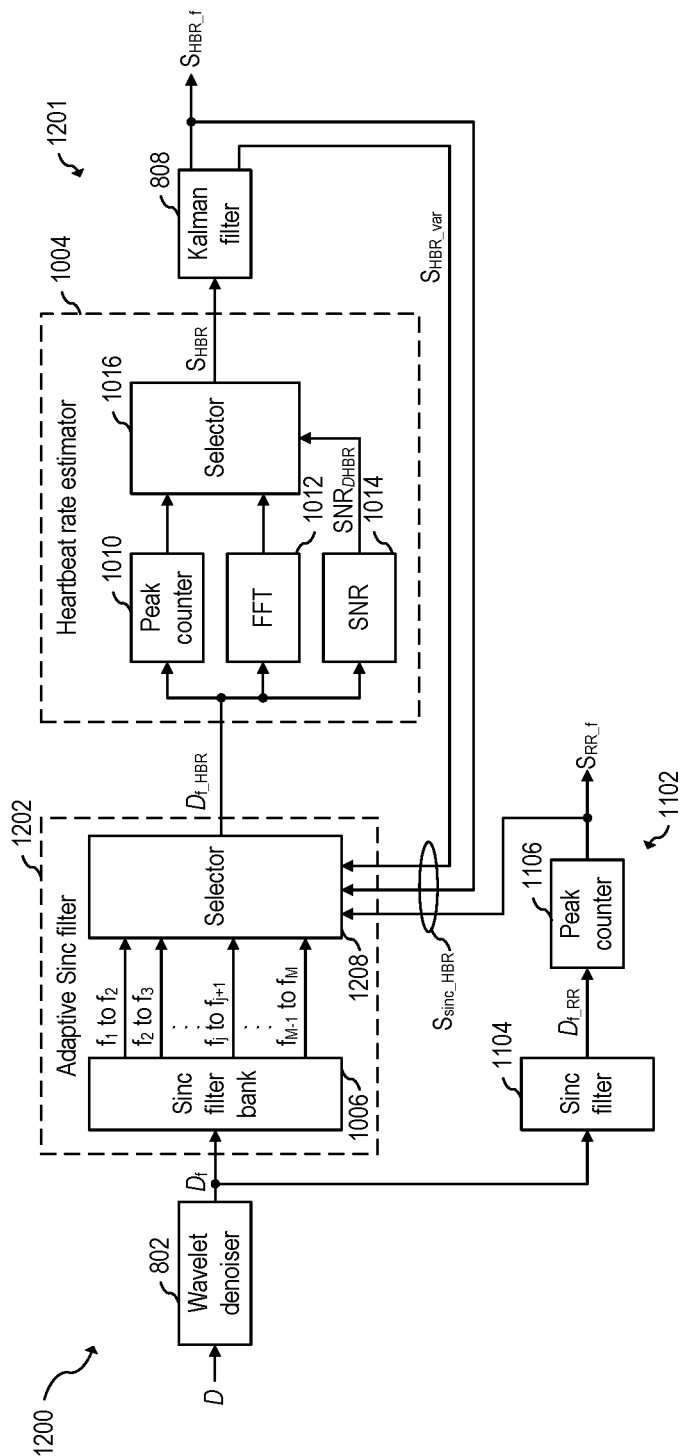

Thus, in some embodiments, the settings of the adaptive Sinc filter are based on the respiration rate $S_{RR\_f}$. For example, FIG. 12 shows a block diagram of embodiment module 1200 for estimating heartbeat rate and respiration rate of a single human target from displacement signal D, according to an embodiment of the present invention. Module 1200 includes heartbeat rate sensing pipeline 1201, respiration rate sensing pipeline 1102, and wavelet denoiser 802. Heartbeat rate sensing pipeline 1201 includes adaptive Sinc filter 1202 and heartbeat rate estimator 1004. Adaptive Sinc filter 1202 includes Sinc filter bank 1006 and selector 1208. Heartbeat rate sensing pipeline 803 may be implemented as heartbeat rate sensing pipeline 1200. Adaptive Sinc filter 804 may be implemented as adaptive Sinc filter 1202. Processing system 104 may implement module 1200.

In some embodiments, the set of outputs available to selector 1208 is based on the respiration rate $S_{RR\_f}$. For example, in some embodiments, if the respiration rate $S_{RR\_f}$ is lower than a predetermined respiration rate threshold $RR_{thres}$, then a low set of outputs of Sinc filter bank 1006 (e.g., from $f_1$ to $f_Q$, Q being greater than 1 and lower than M) is available to selector 1208 to select outputs in a similar manner as selector 1008. If the respiration rate $S_{RR\_f}$ is higher than the predetermined respiration rate threshold $RR_{thres}$, then a high set of outputs of Sinc filter bank 1006 (e.g., from $f_P$ to $f_M$, P being greater than 1 and lower than M, and preferably lower than Q) is available to selector 1208 to select outputs in a similar manner as selector 1008. For example in an embodiment in which each Sinc filter of Sinc filter bank 1006 has the same bandwidth of 0.1 Hz, $f_1$ is equal to 0.7 Hz and $f_M$ is equal to 2 Hz, Q may be 1.4 Hz and P may be 0.9 Hz, and $RR_{thres}$ may be 16 bpm (0.27 Hz). In such embodiment, when the respiration rate $S_{RR\_f}$ is below 16 bpm, only outputs between 0.7 Hz and 1.4 Hz (0.7 Hz to 0.8 Hz, 0.8 Hz to 0.9 Hz, . . . , 1.2 Hz to 1.3 Hz, and 1.3 Hz to 1.4 Hz) are available for selector 1208 to choose from and when the respiration rate $S_{RR\_f}$ is above 16 bpm, only outputs between 0.9 Hz and 2 Hz (0.9 Hz to 1 Hz, 1 Hz to 1.1 Hz, . . . , 1.8 Hz to 1.9 Hz, 1.9 Hz to 2 Hz) are available for selector 1208 to choose from.

In some embodiments, $RR_{thres}$ may be higher than 16 bpm (such as 17 bpm or higher) or lower than 16 bpm (such as 15 bpm or lower). In some embodiments, $RR_{thres}$ is not fixed.

Figure 13:
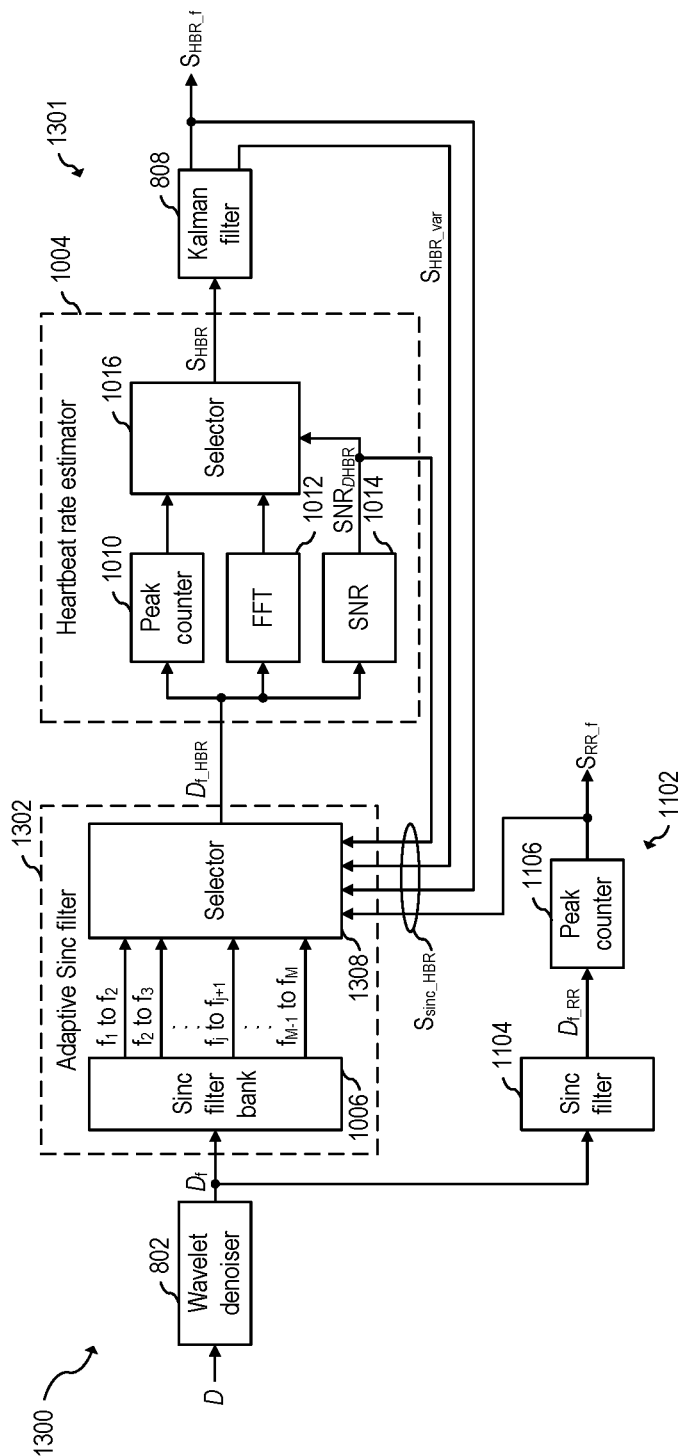

In some embodiments, it is possible that the respiration rate be low (e.g., below $RR_{thres}$) and that the heartbeat rate be outside the bandwidth of the low set of outputs of Sinc filter bank 1006 (e.g., higher than $f_Q$). Thus, in some embodiments, the selection between the low set of outputs and the high set of outputs may be overridden, e.g., based on the SNR $SNR_{DHBR}$ of the displacement signal $D_{f\_HBR}$. For example, FIG. 13 shows a block diagram of embodiment module 1300 for estimating heartbeat rate and respiration rate of a single human target from displacement signal D, according to an embodiment of the present invention. Module 1300 includes heartbeat rate sensing pipeline 1301, respiration rate sensing pipeline 1102, and wavelet denoiser 802. Heartbeat rate sensing pipeline 1301 includes adaptive Sinc filter 1302 and heartbeat rate estimator 1004. Adaptive Sinc filter 1302 includes Sinc filter bank 1006 and selector 1308. Heartbeat rate sensing pipeline 803 may be implemented as heartbeat rate sensing pipeline 1300. Adaptive Sinc filter 804 may be implemented as adaptive Sinc filter 1302. Processing system 104 may implement module 1300.

As shown in FIG. 13, selector 1308 may select one or more outputs of Sinc filter bank 1006 based on heartbeat rate $S_{HBR\_f}$, respiration rate $S_{RR\_f}$, variance $S_{HBR\_var}$, and SNR $SNR_{DHBR}$. For example, if the SNR $SNR_{DHBR}$ (e.g., of the previous estimate) is higher than a predetermined SNR threshold (e.g., $SNR_{thres}$), the respiration rate $S_{RR\_f}$ is below $RR_{thres}$, and the heartbeat rate (e.g., of the previous estimate) is higher than $f_Q$, then selector 1308 selects from the high set of outputs of Sinc filter bank 1006 one or more outputs in a similar manner as selector 1008 (in contrast to selecting from the low set of outputs of Sinc filter bank 1006 if using, e.g., module 1200). For example, in an embodiment in which each Sinc filter of Sinc filter bank 1006 has the same bandwidth of 0.1 Hz, $f_1$ is equal to 0.7 Hz, $f_M$ is equal to 2 Hz, Q is 1.4 Hz, P is 0.9 Hz, and $RR_{thres}$ is 16 bpm (0.27 Hz), if the respiration rate $S_{RR\_f}$ is below 16 bpm, the heartbeat rate $S_{HBR\_f}$ is above 1.4 Hz, and $SNR_{DHBR}$ is above $SNR_{thres}$, then selector 1308 selects from the 12 available outputs of the high set (from 0.9 Hz to 2 Hz) in a similar manner as selector 1008 (e.g., based on $S_{HBR\_var}$ and $S_{HBR\_f}$).

Figure 14:
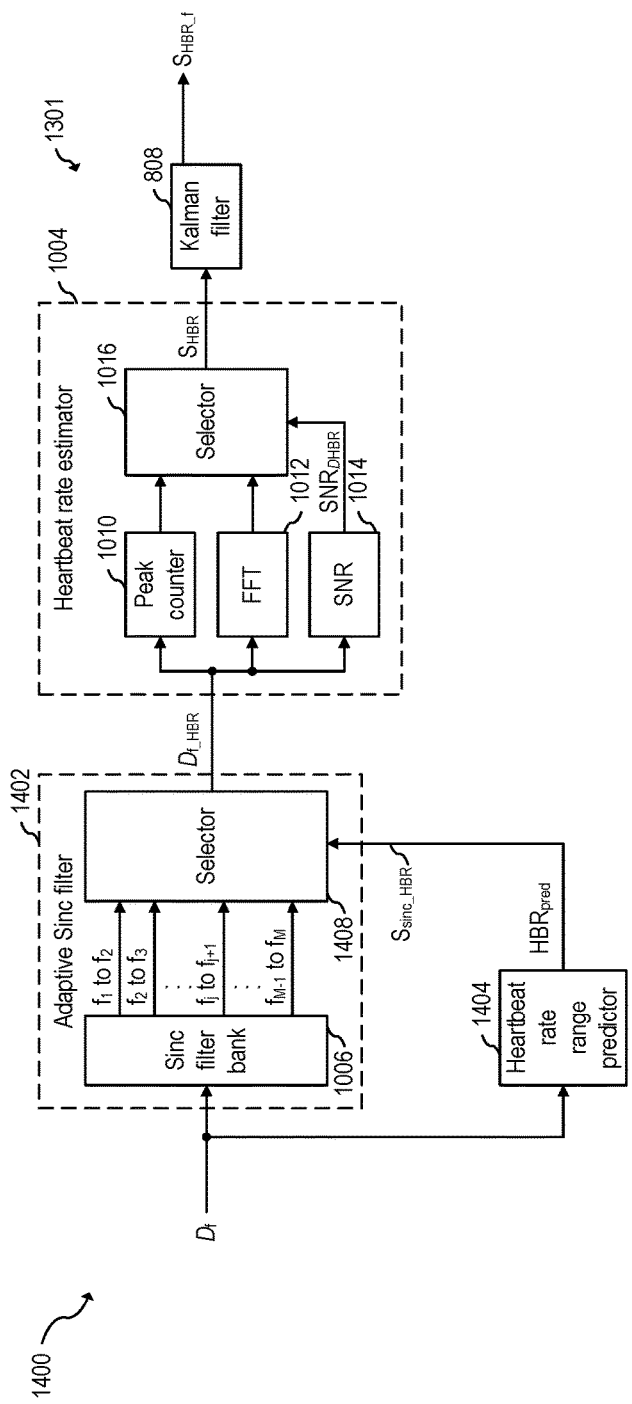
FIG. 14 shows a block diagram of a heartbeat rate sensing pipeline, according to an embodiment of the present invention.

As shown in FIGS. 10-13, the adaptive filter (e.g., 1002, 1102, 1202, 1302) may change its settings based on one or more outputs of Kalman filter 808. Thus, in some embodiments, the adaptive filter (e.g., 1002, 1102, 1202, 1302) may change its settings in a retrospective manner (based on the history of previous heartbeat rate estimates $S_{HBR\_f}$). Some embodiments may change the settings of the adaptive filter in a prospective manner (e.g., based on the current sample $D_f$ and without regard for the previous heartbeat rate estimates $S_{HBR\_f}$). For example, FIG. 14 shows a block diagram of heartbeat rate sensing pipeline 1400, according to an embodiment of the present invention. Heartbeat rate sensing pipeline 1400 includes heartbeat rate range predictor 1404, adaptive Sinc filter 1402, heartbeat rate estimator 1004, and Kalman filter 808. Adaptive Sinc filter 1402 includes Sinc filter bank 1006 and selector 1408. Heartbeat rate sensing pipeline 803 may be implemented as heartbeat rate sensing pipeline 1400. Adaptive Sinc filter 804 may be implemented as adaptive Sinc filter 1402. Processing system 104 may implement heartbeat rate sensing pipeline 1400.

Heartbeat rate range predictor 1404 is configured to predict the frequency range of the heartbeat rate information of the human target based on displacement signal $D_f$. For example, in some embodiments, heartbeat rate range predictor 1404 determines in which range of the M ranges of the M outputs of Sinc filter bank 1006 the heartbeat rate of the human target is based on the displacement signal $D_f$ and provides such frequency range ($HBR_{pred}$) to selector 1402. Selector 1408 then selects one or more outputs of the M outputs of Sinc filter bank 1006 based on the frequency range $HBR_{pred}$. For example, in some embodiments, selector 1408 selects a single output of Sinc filter bank 1006 that corresponds to the frequency range $HBR_{pred}$. In some embodiments, selector 1408 selects more than one output of Sinc filter bank 1006. For example, in some embodiments, selector 1408 selects three outputs of Sinc filter bank 1006, e.g., the output that corresponds to the frequency range $HBR_{pred}$ and the two adjacent outputs (the frequency range above frequency range $HBR_{pred}$ and the frequency range below frequency range $HBR_{pred}$). In some embodiments, the frequency range $HBR_{pred}$ corresponds to a plurality of outputs of Sinc filter bank 1006. Other implementations are also possible.

In some embodiments, heartbeat rate range predictor 1404 is implemented as a classifier with M classes (a class for each of the M ranges of the M outputs of Sinc filter bank 1006). For example, in some embodiments, heartbeat rate range predictor 1404 is implemented as a deep neural network (DNN). The DNN may be trained to predict the frequency ranges of the heartbeat rate based on displacement signal $D_f$. In some embodiments, training the DNN to predict ranges may be advantageously less complex (e.g., may be done in substantially less iterations) than predicting exact values of the heartbeat rate.

As a non-limiting example, in an embodiment in which each Sinc filter of Sinc filter bank 1006 has the same bandwidth of 0.1 Hz, $f_1$ is equal to 0.7 Hz, and $f_M$ is equal to 2 Hz, the DNN of heartbeat rate range predictor 1404 classifies displacement signal $D_f$ as one of 14 possible classes by determining the frequency range $HBR_{pred}$ of the heartbeat rate out of 14 possible frequency ranges (0.7 Hz to 0.8 Hz, 0.8 Hz to 0.9 Hz, . . . , 1.8 Hz to 1.9 Hz, and 1.9 Hz to 2 Hz).

In some embodiments, frequency range $HBR_{pred}$ corresponds to a plurality of outputs (e.g., 2, 3, or more) of Sinc filter bank 1006. Other implementations are also possible.

Figure 15:
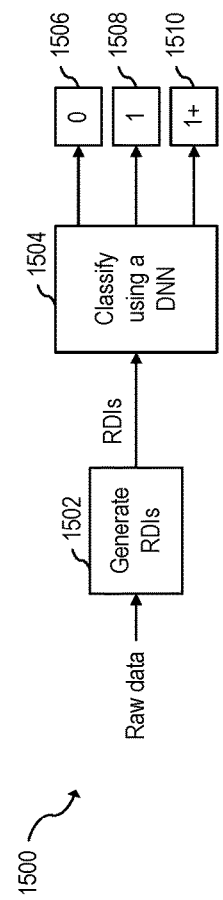
FIG. 15 shows a flow chart of an embodiment method for counting people in a scene, according to an embodiment of the present invention.

FIG. 15 shows a flow chart of embodiment method 1500 for counting people in scene 108, according to an embodiment of the present invention. Step 302 may be performed as method 1500.

During step 1502, raw data is received (e.g., from millimeter-wave radar sensor 102) and RDIs are generated from the received raw data, e.g., in a known manner. For example, in some embodiments, frame integration is performed on the received raw data and MTI filtering is performed on the integrated frames. Then, a range FFT is applied to the integrated and filtered frames using a sliding window and a Doppler FFT is applied on the other corresponding axis to generate a plurality of sequential RDIs. Other implementations are also possible.

During step 1504, a DNN is used to classify the RDIs into 3 possible classes: 0 humans (1506), 1 human (1508), and more than 1 human (1510).

In some embodiments, the DNN used in step 1504 may be trained in a known manner, e.g., using supervised training. By classifying the number of people into 3 classes (1506, 1508, and 1510) instead of counting the exact number of people in scene 108, some embodiments may advantageously train the DNN faster and with less iteration than if determining the exact number of people in scene 108.

In some embodiments, the DNN used in step 1504 may be implemented as a convolutional neural network (CNN) or as a CNN with long short-term memory (LSTM). Other implementations are also possible.

Figure 16:
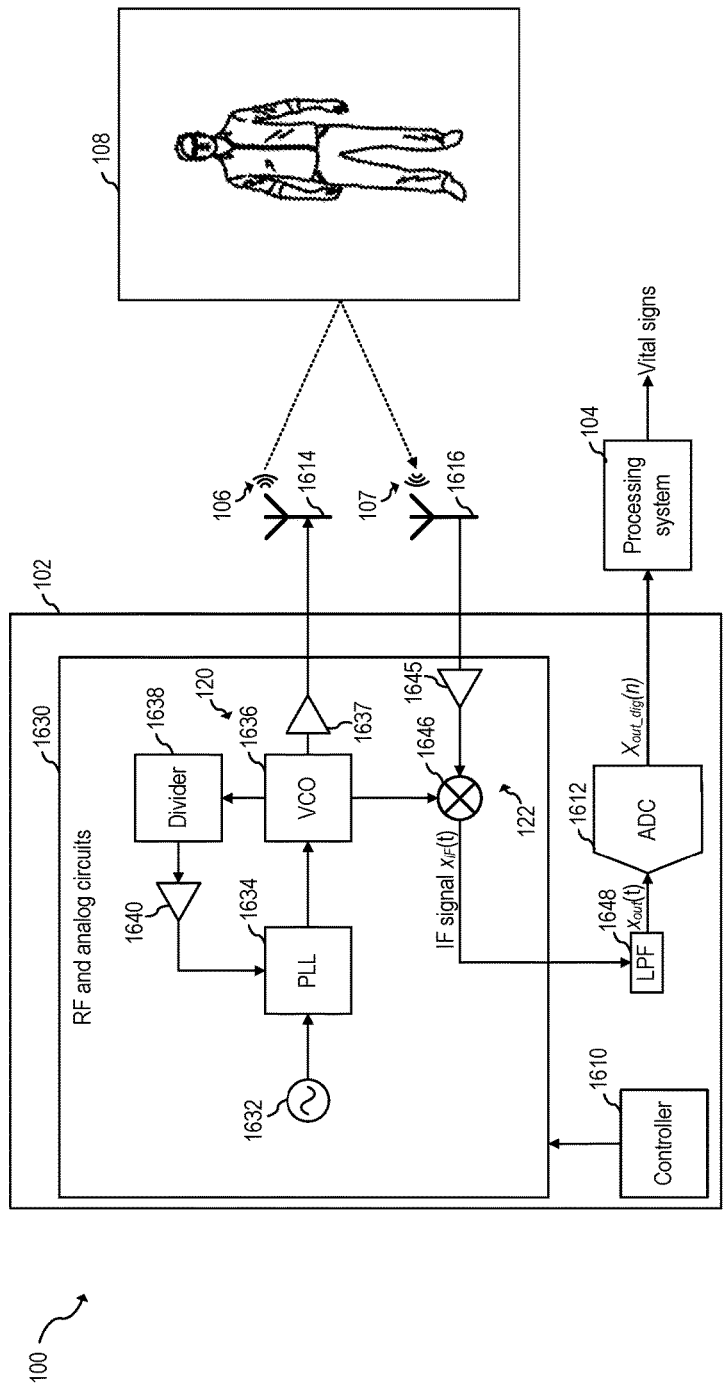
FIG. 16 shows a schematic diagram of a possible implementation of the millimeter-wave radar sensor of FIG. 2, according to an embodiment of the present invention.

FIG. 16 shows a schematic diagram of a possible implementation of millimeter-wave radar sensor 102, according to an embodiment of the present invention. In some embodiments, millimeter-wave radar sensor 102 may be used to generate radar raw data ($x_{out\_dig}(n)$) and provide such raw data to processing system 104 for determining vital signs (e.g., $S_{HBR\_f}$, $S_{RR\_f}$) of a human target.

During normal operation, millimeter-wave radar sensor 102 may operate as a frequency-modulated continuous-wave (FMCW) radar sensor and transmits a plurality of TX radar signals 106, such as chirps, towards scene 108 using one or more transmitter (TX) antenna 1614. The radar signals 106 are generated using RF and analog circuits 1630. The radar signals 106 may be, e.g., in the 20 GHz to 122 GHz range. Other frequencies may also be used.

The radar signals 106 are reflected by objects in scene 108. The reflected radar signals 107, which are also referred to as the echo signal, are received by one or more receiving (RX) antennas 1616. RF and analog circuits 1630 processes the received reflected radar signals 107 using, e.g., bandpass filters (BPFs), low-pass filters (LPFs), mixers, low-noise amplifier (LNA), and/or intermediate frequency (IF) amplifiers in ways known in the art to generate an analog signal $x_{out}(t)$.

The analog signal $x_{out}(t)$ is converted to raw digital data $x_{out\_dig}(n)$ (also referred to as raw radar data or raw data) using ADC 1612. The raw digital data $x_{out\_dig}(n)$ is processed by processing system 104 to, e.g., to determine the vital signs (e.g., $S_{HBR\_f}$, $S_{RR\_f}$) of a human target in scene 108.

Controller 1610 controls one or more circuits of millimeter-wave radar sensor 102, such as RF and analog circuit 1630 and/or ADC 1612. Controller 1610 may be implemented, e.g., as a custom digital or mixed signal circuit, for example. Controller 1610 may also be implemented in other ways, such as using a general purpose processor or controller, for example. In some embodiments, processing system 104 implements a portion or all of controller 1610.

Processing system 104 may be implemented with a general purpose processor, controller or digital signal processor (DSP) that includes, for example, combinatorial circuits coupled to a memory and configured to execute instructions stored in the memory. In some embodiments, processing system 1204 may be implemented as an application specific integrated circuit (ASIC). In some embodiments, processing system 104 may be implemented with an ARM, RISC, or x86 architecture, for example. In some embodiments, processing system 104 may include an artificial intelligence (AI) accelerator. Some embodiments may use a combination of hardware accelerator and software running on a DSP or general purpose microcontroller. In some embodiments, processing system 104 may be implemented with a plurality of processors and/or controllers. Other implementations are also possible.

In some embodiments, millimeter-wave radar sensor 102 and a portion or all of processing system 104 may be implemented inside the same integrated circuit (IC). For example, in some embodiments, millimeter-wave radar sensor 102 and a portion or all of processing system 104 may be implemented in respective semiconductor substrates that are integrated in the same package. In other embodiments, millimeter-wave radar sensor 102 and a portion or all of processing system 104 may be implemented in the same monolithic semiconductor substrate. In some embodiments, millimeter-wave radar sensor 102 and processing system 104 are implemented in respective integrated circuits. In some embodiments, a plurality of integrated circuits is used to implement millimeter-wave radar sensor 102. In some embodiments, a plurality of integrated circuits is used to implement processing system 104. Other implementations are also possible.

As a non-limiting example, RF and analog circuits 1630 may be implemented, e.g., as shown in FIG. 16. During normal operation, voltage-controlled oscillator (VCO) 1636 generates radar signals, such as a linear frequency chirps (e.g., from 57 GHz to 64 GHz, or from 76 GHz to 77 GHz), which are transmitted by transmitting antenna 1614. The VCO 1636 is controlled by PLL 1634, which receives a reference clock signal (e.g., 80 MHz) from reference oscillator 1632. PLL 1634 is controlled by a loop that includes frequency divider 1638 and amplifier 1640. Amplifier 1637 may be used to drive transmitting antenna 1614.

The TX radar signals 106 transmitted by one or more transmitting antennas 1614 are reflected by objects in scene 108 and received by one or more receiving antennas 1616. The echo received by receiving antenna 1616 is mixed with a replica of the signal transmitted by transmitting antenna 1614 using mixer 1646 to produce intermediate frequency (IF) signal $x_{IF}(t)$ (also known as beat signal). In some embodiments, the beat signal $x_{IF}(t)$ has a bandwidth between 10 kHz and 1 MHz. Beat signals with a bandwidth lower than 10 kHz or higher than 1 MHz is also possible. Amplifier 1645 may be used to receive the reflected radar signals from antenna 1616.

Beat signal $x_{IF}(t)$ is filtered with low-pass filters (LPF) 1648 and then sampled by ADC 1612. ADC 1212 is advantageously capable of sampling the filtered beat signal $x_{out}(t)$ with a sampling frequency that is much smaller than the frequency of the signal received by receiving antenna 1616. Using FMCW radars, therefore, advantageously allows for a compact and low cost implementation of ADC 1612, in some embodiments.

The raw digital data $x_{out\_dig}(n)$, which in some embodiments include the digitized version of the filtered beat signal $x_{out}(t)$ is (e.g., temporarily) stored, e.g., in matrices of $N_c \times N_s$ per receiving antenna 1616, where $N_c$ is the number of chirps considered in a frame and $N_s$ is the number of transmit samples per chirp, for further processing by processing system 104.

Figure 17:
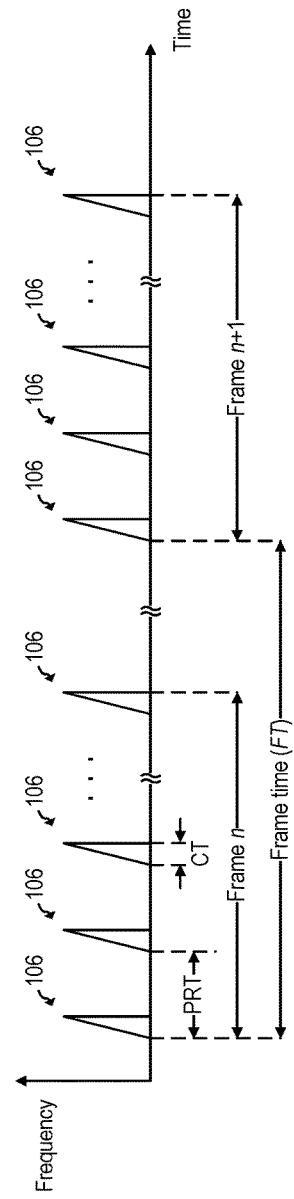
FIG. 17 shows a sequence of chirps transmitted by the transmitting antenna of FIG. 16, according to an embodiment of the present invention.

FIG. 17 shows a sequence of chirps 106 transmitted by TX antenna 1614, according to an embodiment of the present invention. As shown by FIG. 17, chirps 106 are organized in a plurality of frames and may be implemented as up-chirps. Some embodiments may use down-chirps or a combination of up-chirps and down-chirps, such as up-down chirps and down-up chirps. Other waveform shapes may also be used.

As shown in FIG. 17, each frame may include a plurality of chirps 106. For example, in some embodiments, the number of chirps in a frame is 16. Some embodiments may include more than 16 chirps per frame, such as 20 chirps, 32 chirps, or more, or less than 16 chirps per frame, such as 10 chirps, 8 chirps, or less. In some embodiments, each frame includes only a single chirp.

In some embodiments, frames are repeated every FT time. In some embodiments, FT time is 50 ms. A different FT time may also be used, such as more than 50 ms, such as 60 ms, 100 ms, 200 ms, or more, or less than 50 ms, such as 45 ms, 40 ms, or less.

In some embodiments, the FT time is selected such that the time between the beginning of the last chirp of frame n and the beginning of the first chirp of frame n+1 is equal to PRT. Other embodiments may use or result in a different timing.

The time between chirps of a frame is generally referred to as pulse repetition time (PRT). In some embodiments, the PRT is 5 ms. A different PRT may also be used, such as less than 5 ms, such as 4 ms, 2 ms, or less, or more than 5 ms, such as 6 ms, or more.

The duration of the chirp (from start to finish) is generally referred to as chirp time (CT). In some embodiments, the chirp time may be, e.g., 64 μs. Higher chirp times, such as 128 μs, or higher, may also be used. Lower chirp times, may also be used.

In some embodiments, the chirp bandwidth may be, e.g., 4 GHz. Higher bandwidth, such as 6 GHz or higher, or lower bandwidth, such as 2 GHz, 1 GHz, or lower, may also be possible.

In some embodiments, the sampling frequency of millimeter-wave radar sensor 902 may be, e.g., 1 MHz. Higher sampling frequencies, such as 2 MHz or higher, or lower sampling frequencies, such as 500 kHz or lower, may also be possible.

In some embodiments, the number of samples used to generate a chirp may be, e.g., 64 samples. A higher number of samples, such as 128 samples, or higher, or a lower number of samples, such as 32 samples or lower, may also be used.

Figure 18:
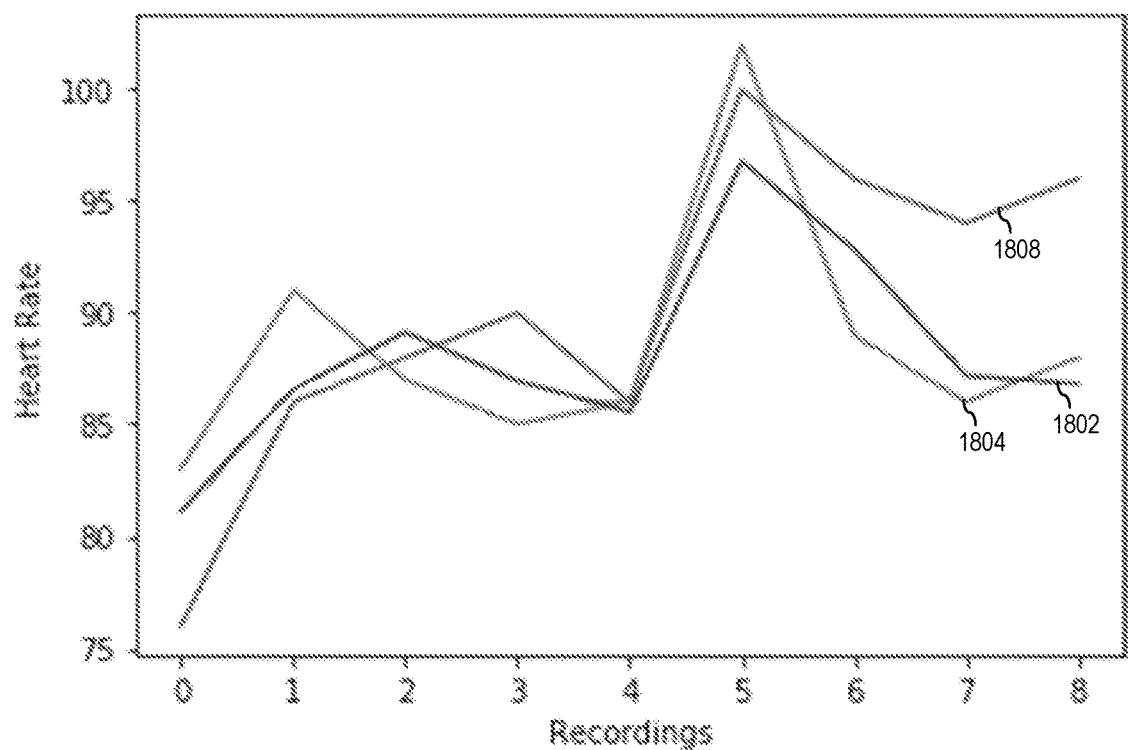
FIGS. 18 and 19 illustrate heartbeat rate estimations of an embodiment compared with the ground truth, according to an embodiment of the present invention.
Figure 19:
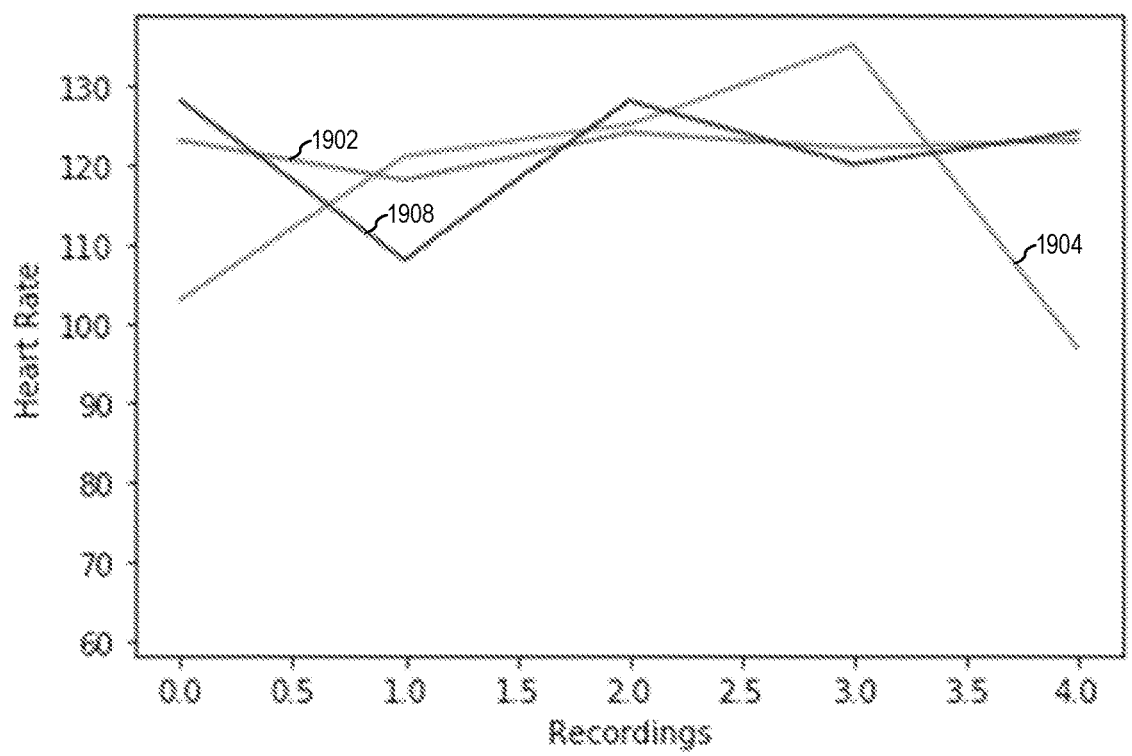

FIGS. 18 and 19 illustrate vital sign outputs of an embodiment compared with the ground truth, according to an embodiment of the present invention. FIG. 18 corresponds to a quasi-static human target while FIG. 19 corresponds to a human target shaking legs and exhibiting RBM.

Curves 1802 and 1902 were generated by performing method 500 to generate the displacement signal D and using heartbeat rate sensing pipeline 1000 to generate the heartbeat rate estimate, with a single human target in front of millimeter-wave radar sensor 102.

Curves 1804 and 1904 were generated using a conventional heartbeat rate sensor attached the human target. Curves 1804 and 1904 serve as ground truth.

Curves 1806 and 1906 were generated using a millimeter-wave radar in a conventional manner.

As shown in FIG. 18, curve 1802 is closer to the ground truth (1804) than using a conventional method (curve 1806). In particular, the RMSE score for curve 1802 is lower (2.9143) than for curve 1806 (5.5877).

Similarly, as shown in FIG. 19, curve 1902 is closer to the ground truth (1904) than using a conventional method (curve 1906). In particular, the RMSE score for curve 1902 is lower (15.8430) than for curve 1906 (187457).

Figure 20:
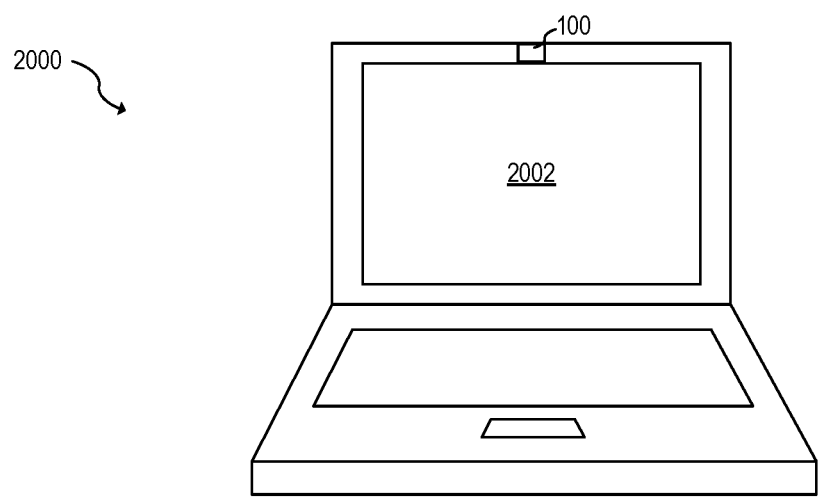
FIG. 20 shows a device, according to an embodiment of the present invention.

FIG. 20 shows device 2000, according to an embodiment of the present invention. Device 2000 includes radar system 100, and screen 2002.

In some embodiments, radar system 100 estimates vital signs (e.g., $S_{HBR\_f}$, $S_{RR\_f}$) of a human sitting in front of screen 2002, and screen 2002 displays such estimated vital signs.

As shown in FIG. 20, device 2000 may be implemented as a laptop. In some embodiments, device 2000 may be implemented, e.g., as a mobile phone, television, etc.

Example embodiments of the present invention are summarized here. Other embodiments can also be understood from the entirety of the specification and the claims filed herein.

Example 1. A method including: transmitting radar signals using a millimeter-wave radar sensor; receiving reflected radar signals using the millimeter-wave radar sensor; generating raw digital data based on the reflected radar signals; generating a target displacement signal indicative of a movement of a human target based on the raw digital data; and estimating a vital sign of the human target based on the target displacement signal, where generating the target displacement signal includes: generating target in-phase (I) and quadrature (Q) (I/Q) data associated with the human target based on the raw digital data, classifying the target I/Q data as high quality data or as low quality data using a first neural network, when the target I/Q data is classified as low quality data, discarding the target I/Q data, when the target I/Q data is classified as high quality data, performing ellipse fitting on the target I/Q data to generate compensated I/Q data, and generating the target displacement signal based on the compensated I/Q data.

Example 2. The method of example 1, where generating the target I/Q data includes: generating preliminary IQ data based on the raw digital data; high-pass filtering the preliminary IQ data to generate a high-pass filtered IQ data using a high-pass cutoff frequency; estimating a power of the high-pass filtered IQ data; when the estimated power is higher than a power threshold, discarding the preliminary IQ data; and when the estimated power is lower than the power threshold, low-pass filtering the preliminary IQ data using a low-pass cutoff frequency to generate the target IQ data.

Example 3. The method of one of examples 1 or 2, where the high-pass cutoff frequency is equal to the low-pass cutoff frequency.

Example 4. The method of one of examples 1 to 3, where classifying the target I/Q data as low quality data includes classifying the target I/Q data as random body movement (RBM) data or as intermodulation product (IMP) data.

Example 5. The method of one of examples 1 to 4, further including performing wavelet denoising on the target displacement signal to generate a denoised displacement signal, where estimating the vital sign of the human target is based on the denoised displacement signal.

Example 6. The method of one of examples 1 to 5, further including performing adaptive Sinc filtering to generate a vital sign filtered displacement signal based on the target displacement signal, where estimating the vital sign of the human target is based on the vital sign filtered displacement signal.

Example 7. The method of one of examples 1 to 6, where performing adaptive Sinc filtering includes generating M Sinc filter outputs using M Sinc filters based on the target displacement signal and generating the vital sign filtered displacement signal based on one or more of the M Sinc filter outputs, where M is a positive integer greater than 1.

Example 8. The method of one of examples 1 to 7, further including filtering the estimated vital sign using a Kalman filter to generate a filtered vital sign.

Example 9. The method of one of examples 1 to 8, further including generating, with the Kalman filter, a vital sign variance associated with the filtered vital sign, where generating the vital sign filtered displacement signal is further based on the filtered vital sign and vital sign variance.

Example 10. The method of one of examples 1 to 9, where the estimated vital sign of the human target is an estimated heartbeat rate of the human target, the method further including estimating a respiration rate of the human target based on the target displacement signal.

Example 11. The method of one of examples 1 to 10, where generating the vital sign filtered displacement signal is further based on the respiration rate.

Example 12. The method of one of examples 1 to 11, where generating the vital sign filtered displacement signal is based on a first sub-set of outputs of the M Sinc filter outputs when the respiration rate is below a respiration rate threshold, and is based on a second sub-set of outputs of the M Sinc filter outputs when the respiration rate is above the respiration rate threshold, the first sub-set of outputs being different from the second sub-set of outputs.

Example 13. The method of one of examples 1 to 12, where the first sub-set of outputs corresponds to outputs of first Sinc filters having adjacent bandwidth, where the second sub-set of outputs corresponds to outputs of second Sinc filters having adjacent bandwidth, and where a low-corner frequency of the collective bandwidth of the first Sinc filters is smaller than a low-corner frequency of the collective bandwidth of the second Sinc filters.

Example 14. The method of one of examples 1 to 13, further including: determining a signal-to-noise (SNR) ratio of the vital sign filtered displacement signal; when the SNR ratio is above an SNR threshold, performing a Fourier transform on the vital sign filtered displacement signal to estimate the vital sign of the human target; and when the SNR ratio is below the SNR threshold, performing peak counting on the vital sign filtered displacement signal to estimate the vital sign of the human target, where generating the vital sign filtered displacement signal is further based on the SNR ratio.

Example 15. The method of one of examples 1 to 14, further including determining a frequency range of the vital sign of the human target based on the target displacement signal using a deep neural network (DNN), where generating the vital sign filtered displacement signal is further based on the frequency range.

Example 16. The method of one of examples 1 to 15, further including generating the vital sign filtered displacement signal based on a plurality of Sinc filter outputs of the M Sinc filter outputs by concatenating the plurality of Sinc filter outputs.

Example 17. The method of one of examples 1 to 16, where each of the M Sinc filters have the same bandwidth.

Example 18. The method of one of examples 1 to 17, where each of the M Sinc filters have fixed corner frequencies.

Example 19. The method of one of examples 1 to 18, further including displaying the estimated vital sign on a screen.

Example 20. The method of one of examples 1 to 19, where a vital sensing pipeline is used for generating the target displacement signal and estimating the vital sign of the human target, the method further including: determining a number of people within a field-of-view of the millimeter-wave radar sensor; when the number of people is equal to 0, disabling the vital sensing pipeline; and when the number of people is equal to 1, enabling the vital sensing pipeline.

Example 21. The method of one of examples 1 to 20, further including: determining a range of the human target; when the human target is closer than a predetermined range and the number of people is higher than 1, asserting a low confidence signal indicative of low confidence in the estimated vital sign and enabling the vital sensing pipeline; and when the human target is closer than the predetermined range and the number of people is higher than 1, disabling the vital sensing pipeline.

Example 22. The method of one of examples 1 to 21, where the first neural network is a SincNet neural network.

Example 23. A radar system including: a millimeter-wave radar sensor including: a transmitter configured to transmit radar signals, a receiver configured to receive reflected radar signals, and an analog-to-digital converter (ADC) configured to generate raw digital data based on the reflected radar signals; and a processing system configured to: generate target in-phase (I) and quadrature (Q) (I/Q) data associated with a human target based on the raw digital data, classify the target I/Q data as high quality data or as low quality data using a first neural network, when the target I/Q data is classified as low quality data, discard the target I/Q data, when the target I/Q data is classified as high quality data, perform ellipse fitting on the target I/Q data to generate compensated I/Q data, generate a target displacement signal indicative of a movement of the human target, and estimate a heartbeat rate of the human target based on the target displacement signal.

Example 24. A method including: transmitting radar signals using a millimeter-wave radar; receiving reflected radar signals using the millimeter-wave radar; generating raw digital data based on the reflected radar signals; generating a target displacement signal indicative of a movement of a human target based on the raw digital data; performing wavelet denoising on the target displacement signal to generate a denoised displacement signal; using an adaptive Sinc filter to generate a heartbeat filtered displacement signal based on the denoised displacement signal; and estimating a heartbeat rate of the human target based on the heartbeat filtered displacement signal.

Example 25. A method including: transmitting radar signals using a millimeter-wave radar sensor; receiving reflected radar signals using the millimeter-wave radar sensor; generating raw digital data based on the reflected radar signals; determining a number of people within a field-of-view of the millimeter-wave radar sensor based on the raw digital data; when the number of people is equal to 1, using a vital sensing pipeline to generate a target displacement signal indicative of a movement of a human target based on the raw digital data, and estimate a vital sign of the human target based on the target displacement signal; and when the number of people is greater equal to 0, disabling the vital sensing pipeline.

Example 26. The method of example 25, further including, when the number of people is equal to 1, determining a target range associated with the human target; when the target range is higher than a range threshold, disabling the vital sensing pipeline; and when the target range is lower than the range threshold, using the vital sensing pipeline to generate the target displacement signal and estimate a vital sign of the human target based on the target displacement signal, and asserting a low confidence signal indicative of low confidence in the estimated vital sign.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method comprising:
   transmitting radar signals using a millimeter-wave radar sensor;
   receiving reflected radar signals using the millimeter-wave radar sensor;
   generating raw digital data based on the reflected radar signals;
   generating a target displacement signal indicative of a movement of a human target based on the raw digital data; and
   estimating a vital sign of the human target based on the target displacement signal, wherein generating the target displacement signal comprises:
   generating target in-phase (I) and quadrature (Q) (I/Q) data associated with the human target based on the raw digital data,
   classifying the target I/Q data as high quality data or as low quality data using a first neural network,
   when the target I/Q data is classified as low quality data, discarding the target I/Q data,
   when the target I/Q data is classified as high quality data, performing ellipse fitting on the target I/Q data to generate compensated I/Q data, and
   generating the target displacement signal based on the compensated I/Q data; and
   performing adaptive Sinc filtering to generate a vital sign filtered displacement signal based on the target displacement signal, wherein estimating the vital sign of the human target is based on the vital sign filtered displacement signal.

2. The method of claim 1, wherein generating the target I/Q data comprises:
   generating preliminary I/Q data based on the raw digital data;
   high-pass filtering the preliminary I/Q data to generate a high-pass filtered I/Q data using a high-pass cutoff frequency;
   estimating a power of the high-pass filtered I/Q data;
   when the estimated power is higher than a power threshold, discarding the preliminary I/Q data; and
   when the estimated power is lower than the power threshold, low-pass filtering the preliminary I/Q data using a low-pass cutoff frequency to generate the target I/Q data.

3. The method of claim 2, wherein the high-pass cutoff frequency is equal to the low-pass cutoff frequency.

4. The method of claim 1, wherein classifying the target I/Q data as low quality data comprises classifying the target I/Q data as random body movement (RBM) data or as intermodulation product (IMP) data.

5. The method of claim 1, further comprising performing wavelet denoising on the target displacement signal to generate a denoised displacement signal, wherein estimating the vital sign of the human target is based on the denoised displacement signal.

6. The method of claim 1, wherein performing adaptive Sinc filtering comprises generating M Sinc filter outputs using M Sinc filters based on the target displacement signal and generating the vital sign filtered displacement signal based on one or more of the M Sinc filter outputs, wherein M is a positive integer greater than 1.

7. The method of claim 6, further comprising filtering the estimated vital sign using a Kalman filter to generate a filtered vital sign.

8. The method of claim 7, further comprising generating, with the Kalman filter, a vital sign variance associated with the filtered vital sign, wherein generating the vital sign filtered displacement signal is further based on the filtered vital sign and the vital sign variance.

9. The method of claim 6, wherein the estimated vital sign of the human target is an estimated heartbeat rate of the human target, the method further comprising estimating a respiration rate of the human target based on the target displacement signal.

10. The method of claim 9, wherein generating the vital sign filtered displacement signal is further based on the respiration rate.

11. The method of claim 10, wherein generating the vital sign filtered displacement signal is based on a first sub-set of outputs of the M Sinc filter outputs when the respiration rate is below a respiration rate threshold, and is based on a second sub-set of outputs of the M Sinc filter outputs when the respiration rate is above the respiration rate threshold, the first sub-set of outputs being different from the second sub-set of outputs.

12. The method of claim 11, wherein the first sub-set of outputs corresponds to outputs of first Sinc filters having adjacent bandwidth, wherein the second sub-set of outputs corresponds to outputs of second Sinc filters having adjacent bandwidth, and wherein a low-corner frequency of a collective bandwidth of the first Sinc filters is smaller than a low-corner frequency of a collective bandwidth of the second Sinc filters.

13. The method of claim 10, further comprising:
determining a signal-to-noise ratio (SNR) of the vital sign filtered displacement signal;
when the SNR is above an SNR threshold, performing a Fourier transform on the vital sign filtered displacement signal to estimate the vital sign of the human target; and
when the SNR is below the SNR threshold, performing peak counting on the vital sign filtered displacement signal to estimate the vital sign of the human target, wherein generating the vital sign filtered displacement signal is further based on the SNR.

14. The method of claim 6, further comprising determining a frequency range of the vital sign of the human target based on the target displacement signal using a deep neural network (DNN), wherein generating the vital sign filtered displacement signal is further based on the frequency range.

15. The method of claim 6, further comprising generating the vital sign filtered displacement signal based on a plurality of Sinc filter outputs of the M Sinc filter outputs by concatenating the plurality of Sinc filter outputs.

16. The method of claim 6, wherein each of the M Sinc filters has the same bandwidth.

17. The method of claim 6, wherein each of the M Sinc filters has a fixed corner frequency.

18. The method of claim 1, further comprising displaying the estimated vital sign on a screen.

19. The method of claim 1, wherein a vital sensing pipeline is used for generating the target displacement signal and estimating the vital sign of the human target, the method further comprising:
determining a number of people within a field-of-view of the millimeter-wave radar sensor;
when the number of people is equal to 0, disabling the vital sensing pipeline; and
when the number of people is equal to 1, enabling the vital sensing pipeline.

20. The method of claim 19, further comprising:
determining a range of the human target;
when the human target is closer than a predetermined range and the number of people is higher than 1, asserting a low confidence signal indicative of low confidence in the estimated vital sign and enabling the vital sensing pipeline; and
when the human target is higher than the predetermined range and the number of people is higher than 1, disabling the vital sensing pipeline.

21. The method of claim 1, wherein the first neural network is a SincNet neural network.

22. A radar system comprising:
a millimeter-wave radar sensor comprising:
a transmitter configured to transmit radar signals,
a receiver configured to receive reflected radar signals, and
an analog-to-digital converter (ADC) configured to generate raw digital data based on the reflected radar signals; and
a processing system configured to:
generate target in-phase (I) and quadrature (Q) (I/Q) data associated with a human target based on the raw digital data,
classify the target I/Q data as high quality data or as low quality data using a first neural network,
when the target I/Q data is classified as low quality data, discard the target I/Q data,
when the target I/Q data is classified as high quality data, perform ellipse fitting on the target I/Q data to generate compensated I/Q data,
generate a target displacement signal indicative of a movement of the human target based on the compensated I/Q data,
estimate a vital sign of the human target based on the target displacement signal, and
perform adaptive Sinc filtering to generate a vital sign filtered displacement signal based on the target displacement signal, wherein estimating the vital sign of the human target is based on the vital sign filtered displacement signal.

23. A method comprising:
transmitting radar signals using a millimeter-wave radar sensor;
receiving reflected radar signals using the millimeter-wave radar sensor;
generating raw digital data based on the reflected radar signals;

generating a target displacement signal indicative of a movement of a human target based on the raw digital data; and estimating a vital sign of the human target based on the target displacement signal, wherein generating the target displacement signal comprises:

generating target in-phase (I) and quadrature (Q) (I/Q) data associated with the human target based on the raw digital data, generating the target I/Q data comprising:

generating preliminary I/Q data based on the raw digital data, high-pass filtering the preliminary I/Q data to generate a high-pass filtered I/Q data using a high-pass cutoff frequency, estimating a power of the high-pass filtered I/Q data, when the estimated power is higher than a power threshold, discarding the preliminary I/Q data, and when the estimated power is lower than the power threshold, low-pass filtering the preliminary I/Q data using a low-pass cutoff frequency to generate the target I/Q data, classifying the target I/Q data as high quality data or as low quality data using a first neural network, when the target I/Q data is classified as low quality data, discarding the target I/Q data, when the target I/Q data is classified as high quality data, performing ellipse fitting on the target I/Q data to generate compensated I/Q data, and generating the target displacement signal based on the compensated I/Q data.

24. The method of claim 23, wherein the high-pass cutoff frequency is equal to the low-pass cutoff frequency.

* * * * *